United States Patent
Ohkawa et al.

[11] Patent Number: 5,866,567
[45] Date of Patent: Feb. 2, 1999

[54] DIAZEPINONES, THEIR PRODUCTION AND USE

[75] Inventors: Shigenori Ohkawa; Nobuhiro Fujii, both of Osaka; Koichi Kato, Ibaraki, all of Japan

[73] Assignee: Takeda Chemical Industries, Ltd., Osaka, Japan

[21] Appl. No.: 666,430

[22] PCT Filed: May 30, 1996

[86] PCT No.: PCT/JP96/01463

§ 371 Date: Jun. 25, 1996

§ 102(e) Date: Jun. 25, 1996

[87] PCT Pub. No.: WO96/38438

PCT Pub. Date: Dec. 5, 1996

[30] Foreign Application Priority Data

Jun. 1, 1995 [JP] Japan ................... 7-135376

[51] Int. Cl.$^6$ .................. C07D 403/06; A61K 31/55
[52] U.S. Cl. ........................... 514/220; 540/495
[58] Field of Search ............... 540/495; 514/220

[56] References Cited

U.S. PATENT DOCUMENTS 4,678,784  7/1987  Ho ............................................ 514/219

FOREIGN PATENT DOCUMENTS 54-135788  10/1979  Japan .
17075  8/1994  WIPO .
29900  11/1995  WIPO .

*Primary Examiner*—Mark L. Berch
*Attorney, Agent, or Firm*—Fitzpatrick, Cella, Harper & Scinto

[57] ABSTRACT

A compound of the general formula

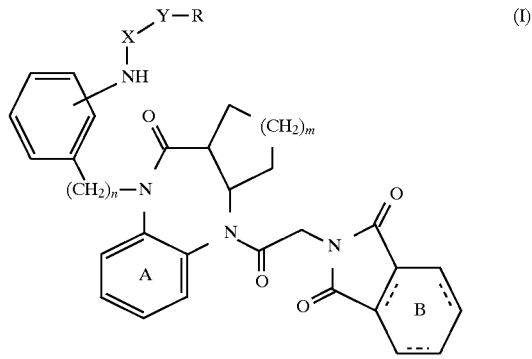

wherein A represents a benzene ring, B represents a 6-membered hydrocarbon ring; X represents a lower alkylene, carbonyl or sulfonyl; Y represents a bond, oxygen or >N—$R^1$, $R^1$ represents H or an alkyl group, R represents H, an aromatic group, or an alkyl group optionally substituted by an aromatic group; m and n each represents 1–3, or a salt thereof has potent GnRH receptor antagonizing activity.

30 Claims, No Drawings

DIAZEPINONES, THEIR PRODUCTION AND USE

This application is a national stage application under 35 U.S.C. § 371 of Pct application No. JP96/01463.

TECHNICAL FIELD

The present invention relates to novel diazepinone compounds and salts having excellent gonadotropin releasing hormone (GnRH) receptor antagonist activity, processes for producing them, and use.

BACKGROUND ART

GnRH is a decapeptide, a peptide consisting of 10 amino acids, which is produced in the hypothalamus and modulates the secretion of luteinizing hormone (LH), follicle stimulating hormone (FSH), etc. via receptors supposedly present in the anterior lobe of the pituitary gland to thereby exhibit multi-pronged physiological activity inclusive of induction of ovulation. Therefore, selective antagonists and agonists specific for such receptors modulate the activities of GnRH hormones produced in the hypothalamus and control secretion of the anterior pituitary hormones such as LH and FSH. As a consequence, the secretion of estrogen in women and of testosterone in men is suppressed. Therefore, these agonists and antagonists can be expected to be clinically useful for the prevention or treatment of gonadotropin-dependent diseases.

Since the discovery of GnRH in 1971, leuprolerin acetate and many other peptides have been synthesized in anticipation of their utility as agonists or antagonists of GnRH. Leuprolerin acetate, which is 20–50 times as active as native GnRH, causes the so-called receptor down-regulation on repeated administration to diminish the release of gonadotropins in the pituitary gland, reduce the response of the testes to gonadotropins to cut down on the production of testosterone to the castrated level, and reduce the productivity of estrogen in the ovaries. As a consequence, the compound exhibits antitumoral efficacy in cancers dependent on such hormones, typically prostate cancer. In fact, leuprolerin acetate is in broad use clinically as a therapeutic agent for prostate cancer, endometriosis, and precocious puberty. It has also been demonstrated that the compound is effective in the treatment of hysteromyoma and breast cancer as well.

However, these GnRH agonists are not well absorbed after oral administration because of their peptide structures, thus imposing restrictions on the dosage form. Moreover, these compounds show a burst of agonist activity following commencement of therapy, elevating blood steroid hormone levels and, hence, causing transient exacerbations, e.g. of bone ache, before the onset of expected therapeutic effects.

Meanwhile, as a tricyclic compound, JP-A-54 135788 discloses that a compound of the formula:

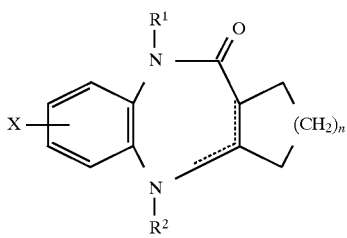

wherein X represents halogen, lower alkyl or lower alkoxy; n is 1 or 2; $R^1$ and $R^2$ may be the same or different and each represents H or lower alkyl; either one of the two bonds represented by dotted lines is a double bond but, when $R^2$ is lower alkyl, it is bound to the nitrogen atom not forming a double bond; and where X and $R^1$ represent H and n is equal to 1, $R^2$ is lower alkyl, has anxiolytic and analgesic actions. Furthermore, WO94/17075 discloses that a compound of the formula:

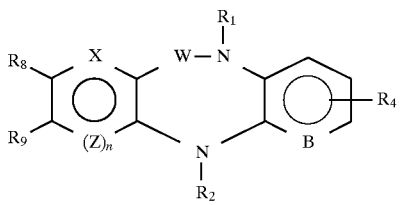

wherein n is 0 or 1, X typically represents =CH, Z represents nitrogen which may be substituted typically by alkyl; W typically represents C=O; $R^1$ and $R_2$ each typically represents hydrogen, benzyl or $C_{2-6}$ alkylacyl; $R_8$, $R_9$ and $R_4$ each typically represents hydrogen, is useful as an antiviral agent.

However, none of the compounds ever discovered are medicinally useful GnRH receptor antagonists and the development of a therapeutically useful compound having improved GnRH receptor antagonist activity with a low risk of side effect has been awaited.

DISCLOSURE OF INVENTION

The inventors of the present invention synthesized a compound [hereinafter referred to briefly as compound (I)] having a basal structure of 1,5-benzodiazepine and, in the 1-position thereof, a substituent comprising an aromatic or heteroaromatic ring substituted by a substituted amino group having a defined chemical structure as represented by the following formula (I), as well as a salt thereof, for the first time and discovered that this compound has excellent GnRH receptor antagonist activity with a low toxic potential and is, therefore, clinically useful.

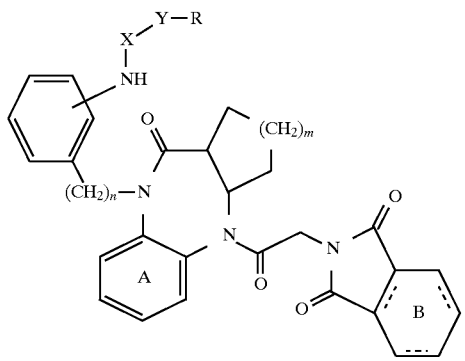

(I)

wherein Ring A represents an optionally substituted benzene ring;

Ring B represents an optionally substituted 6-membered hydrocarbon ring;

- - - represents a single bond or a double bond;

X represents a lower alkylene, carbonyl or sulfonyl;

Y represents a bond, oxygen, lower alkyleneoxy or a group of the formula: $>N-R^1$ wherein $R^1$ represents hydrogen or an alkyl group;

R represents i) hydrogen, ii) an optionally substituted aromatic group or iii) an alkyl group optionally substituted by an optionally substituted aromatic group; and m and n independently represents an integer of 1 to 3

The present invention, therefore, is directed to:

(1) Compound (I) or a salt thereof;

(2) A compound of the above (1) wherein X is a methylene, carbonyl or sulfonyl and Y is a bond, oxygen, methyleneoxy or a group of the formula: $>N-R^1$ wherein $R^1$ is as defined above;

(3) A compound of the above (1) wherein Ring A is a benzene ring optionally substituted by 1 to 5 substituents selected from the group consisting of an amino, mono-$C_{1-6}$ alkylamino, di-$C_{1-6}$ alkylamino, halogen, nitro, sulfo, cyano, hydroxy, $C_{1-6}$ alkyl, $C_{1-6}$ alkoxy, carboxy, $C_{1-6}$ alkoxycarbonyl, $C_{1-5}$ acyl, mercapto and $C_{1-6}$ alkylmercapto, Ring B is a benzene, cyclohexene or cyclohexane group, each of which may be substituted by 1 to 5 substituents selected from the group consisting of an amino, mono-$C_{1-6}$ alkylamino, di-$C_{1-6}$ alkylamino, halogen, nitro, sulfo, cyano, hydroxy, $C_{1-6}$ alkyl, $C_{1-6}$ alkoxy, carboxy, $C_{1-6}$ alkoxycarbonyl, $C_{1-5}$ acyl, mercapto and $C_{1-6}$ alkylmercapto, X is a $C_{1-6}$ alkylene, carbonyl or sulfonyl, Y is a bond, oxygen, $C_{1-6}$ alkyleneoxy or a group of the formula: $>N-R^1$, $R^1$ is hydrogen or a $C_{1-6}$ alkyl group, and R is i) hydrogen, ii) (a) a $C_{6-14}$ aryl group or (b) a 5- to 10-membered heteroaromatic group containing, besides carbon atom(s), 1 to 4 hetero atoms selected from nitrogen, oxygen and sulfur, each of which groups (a) and (b) may be substituted by 1 to 5 substituents selected from the group consisting of an amino, mono-$C_{1-6}$ alkylamino, di-$C_{1-6}$ alkylamino, halogen, nitro, sulfo, cyano, hydroxy, $C_{1-6}$ alkyl, $C_{1-6}$ alkoxy, carboxy, $C_{1-6}$ alkoxycarbonyl, $C_{1-5}$ acyl, mercapto, $C_{1-6}$ alkylmercapto, $C_{6-10}$ aryl and oxo, or iii) a $C_{1-6}$ alkyl group optionally substituted by 1 to 5 substituents selected from the group consisting of (a) a $C_{6-14}$ aryl group and (b) a 5- to 10-membered heteroaromatic group containing, besides carbon atoms, 1 to 4 hetero atoms selected from nitrogen, oxygen and sulfur, each of which groups (a) and (b) may be substituted by 1 to 5 substituents selected from the group consisting of amino, mono-$C_{1-6}$ alkylamino, di-$C_{1-6}$ alkylamino, halogen, nitro, sulfo, cyano, hydroxy, $C_{1-6}$ alkyl, $C_{1-6}$ alkoxy, carboxy, $C_{1-6}$ alkoxycarbonyl, $C_{1-5}$ acyl, mercapto, $C_{1-6}$ alkylmercapto, $C_{6-10}$ aryl and oxo;

(4) A compound of the above (1) wherein Ring A is an unsubstituted benzene ring;

(5) A compound of the above (1) wherein Ring B is an unsubstituted 6-membered hydrocarbon ring;

(6) A compound of the above (5) wherein the hydrocarbon ring is a benzene ring or a cyclohexene ring;

(7) A compound of the above (1) wherein the aromatic group is a phenyl group or a pyridyl group;

(8) A compound of the above (1) wherein R is i) a phenyl or naphthyl group optionally substituted by 1 to 3 substituents selected from the group consisting of a halogen and $C_{1-6}$ alkoxy or ii) a $C_{1-6}$ alkyl group optionally substituted by 1 to 3 substituents selected from the group consisting of a phenyl and pyridyl group, each of which may be substituted by 1 to 3 substituents selected from the group consisting of a halogen and $C_{1-6}$ alkoxy;

(9) A compound of the above (1) wherein X is carbonyl;

(10) A compound of the above (1) wherein Y is oxygen or the group of the formula: $>N-R^1$ wherein $R^1$ is as defined above;

(11) A compound of the above (1) wherein Y is >NH;

(12) A compound of the above (1) wherein the group of the formula: $-NH-X-Y-R$ is present in the 3- or 4-position of the benzene ring;

(13) A compound of the above (1) wherein m is 1;

(14) A compound of the above (1) wherein n is 1;

(15) A compound of the above (1) wherein Ring A is benzene ring,

Ring B is a benzene ring or a cyclohexene ring,

X is a methylene, carbonyl or sulfonyl,

Y is a bond, oxygen, methyleneoxy or a group of the formula: $>N-R^1$, $R^1$ is hydrogen or a $C_{1-6}$ alkyl group, and R is i) a phenyl or naphthyl group optionally substituted by 1 to 3 substituents selected from the group consisting of a halogen and $C_{1-6}$ alkoxy, or ii) a $C_{1-6}$ alkyl group optionally substituted by 1 to 3 substituents selected from the group consisting of a phenyl and pyridyl group which may be substituted by 1 to 3 substituents selected from the group consisting of a halogen and $C_{1-6}$ alkoxy;

(16) A compound of the above (1) which is (3aR*,10aS*)-9-[4-(benzyloxycarbonylamino)benzyl]-4-(2H-1,3-dioxo-1,3,4,5,6,7-hexahydroisoindole-2-acetyl)-2,3,3a,4,9,10a-hexahydrobenzo[b]cyclopenta[e][1,4]diazepin-10(1H)-one or a salt thereof;

(17) A compound of the above (1) which is (3aR*,10aS*)-9-[4-(3-benzylureido)benzyl]-4-(phthalimidoacetyl)-2,3,3a,4,9,10a-hexahydrobenzo[b]cyclopenta[e][1,4]diazepin-10(1H)-one or a salt thereof;

(18) A compound of the above (1) which is (3aR*,10aS*)-9-[4-(3-benzylureido)benzyl]-4-(2H-1,3-dioxo-1,3,4,5,6,7-hexahydroisoindole-2-acetyl)-2,3,3a,4,9,10a- hexahydrobenzo[b]-cyclopenta[e][1,4]diazepin-10 (1H)-one or a salt thereof;

(19) A compound of the above (1) which is (3aR*,10aS*)-9-[4-[3-((R)-1-phenylethyl)ureido]benzyl]-4-(phthalimidoacetyl)-2,3,3a,4,9,10a-hexahydrobenzo[b]cyclopenta[e][1,4]diazepin-10(1H)-one or a salt thereof;

(20) A compound of the above (1) which is (3aR*,10aS*)-9-[4-[3-(2-phenylethyl)ureido]benzyl]-4-(phthalimidoacetyl)-2,3,3a,4,9,10a-hexahydrobenzo[b]cyclopenta[e][1,4]diazepin-10(1H)-one or a salt thereof;

(21) A compound of the above (1) which is (3aR*,10aS*)-9-[4-[3-(4-fluorobenzyl)ureido]benzyl]-4-(phthalimidoacetyl)-2,3,3a, 4,9,10a-hexahydrobenzo[b]cyclopenta[e][1,4]diazepin-10(1H)-one or a salt thereof;

(22) A compound of the above (1) which is (3aR*,10aS*)-9-[4-[3-(4-methoxybenzyl)ureido]benzyl]-4-(phthalimidoacetyl)-2,3,3a,4,9,10a-hexahydrobenzo[b]cyclopenta[e][1,4]diazepin-10(1H)-one or a salt thereof;

(23) A compound of the above (1) which is (3aR*,10aS*)-4-(phthalimidoacetyl)-9-[4-[3-(4-pyridylmethyl)ureido]-benzyl]-2,3,3a,4,9,10a-hexahydrobenzo[b]cyclopenta[e]-[1,4]diazepin-10(1H)-one or a salt thereof;

(24) A process for producing the compound of the above (1) which comprises one of the following steps:

i) a step of reacting a compound of the formula:

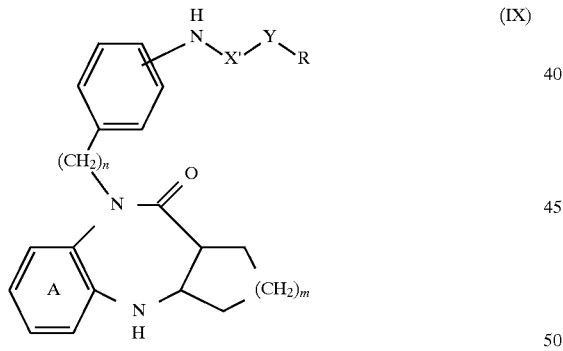

(IX)

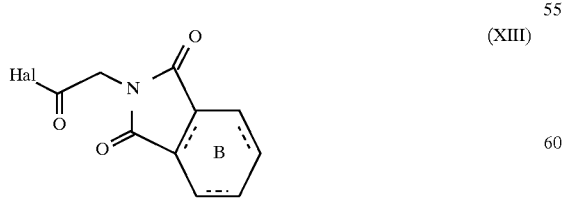

(XIII)

wherein Hal represents halogen and the other symbols are as defined above or a salt thereof, ii) a step of reacting a compound of the formula:

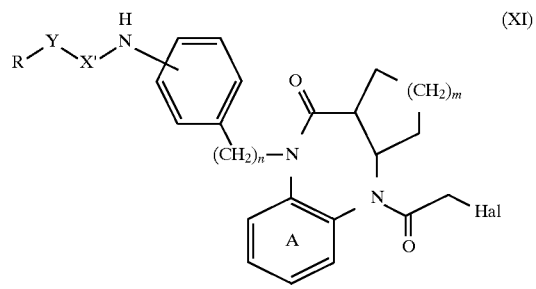

(XI)

wherein each symbol is as defined above or a salt thereof with a compound of the formula:

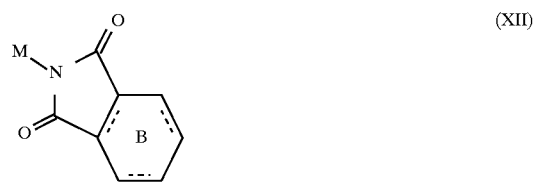

(XII)

wherein M represents a metal and the other symbols are as defined above or a salt thereof, iii) a step of reacting a compound of the formula:

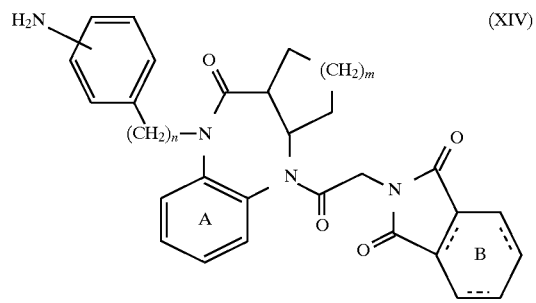

(XIV)

wherein each symbol is as defined above or a salt thereof with a compound of the formula:

(XV)

wherein each symbol is as defined above or a salt thereof, iv) a step of reacting a compound of the formula:

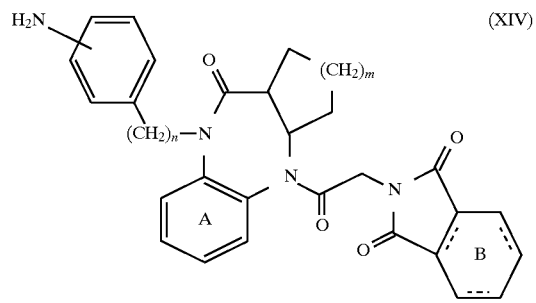

(XIV)

wherein each symbol is as defined above or a salt thereof with a compound of the formula:

(XVI)

wherein X' represents carbonyl or sulfonyl and the other symbols are as defined above or a salt thereof with a compound of the formula:

wherein each symbol is as defined above or a salt thereof in the presence of a reducing agent, v) a step of reacting a compound of the formula:

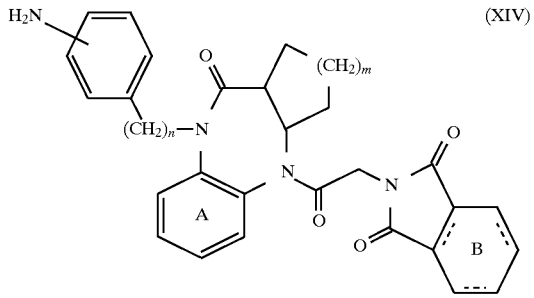
(XIV)

wherein each symbol is as defined above or a salt thereof with a compound of the formula:

RNCO     (XVII)

wherein R is as defined above or a salt thereof, and vi) a step of reacting a compound of the formula:

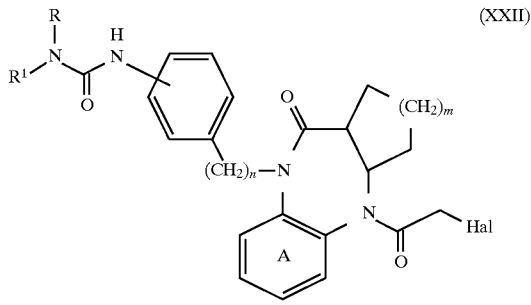
(XXII)

wherein each symbol is as defined above or a salt thereof with a compound of the formula:

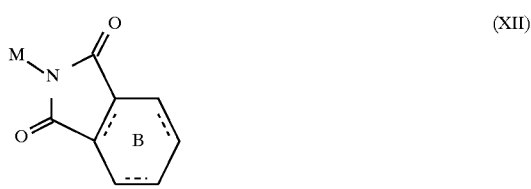
(XII)

wherein each symbol is as defined above or a salt thereof;

and the optional step of subjecting the resultant compound to any one or more of deprotection reaction, acylation reaction, hydrogenation reaction, oxidation reaction, carbon chain extending reaction and substituent-exchange reaction;

(25) A pharmaceutical composition which comprises a compound of the above (1), if necessary together with a pharmaceutically acceptable carrier;

(26) A composition of the above (25) which is a gonadotropin releasing hormone receptor antagonistic composition;

(27) A composition of the above (26) which is for sex hormone dependent diseases;

(28) A composition of the above (27) which is for treating tumors;

(29) A composition of the above (26) which is for controlling fertility; and

(30) A composition of the above (26) which is for controlling menstrual cycle.

The substituent which may be present on the benzene ring of the "optionally substituted benzene ring", represented by Ring A, includes but is not limited to amino, mono-$C_{1-6}$ alkylamino (e.g. methylamino, ethylamino, n-propylamino, n-butylamino, etc.), di-$C_{1-6}$ alkylamino (e.g. dimethylamino, diethylamino, methylethylamino, etc.), halogen (e.g. fluorine, chlorine, bromine, iodine etc.), nitro, sulfo, cyano, hydroxy, $C_{1-6}$ alkyl (e.g. methyl, ethyl, propyl, isopropyl, butyl, isobutyl, sec-butyl, tert-butyl, pentyl, hexyl, etc.), $C_{1-6}$ alkoxy (e.g. methoxy, ethoxy, propoxy, isopropoxy, butoxy, pentyloxy, etc.), carboxy, $C_{1-6}$ alkoxycarbonyl (e.g. methoxycarbonyl, ethoxycarbonyl, propoxycarbonyl, isopropoxycarbonyl, butoxycarbonyl, etc.), $C_{1-5}$ acyl (e.g. formyl, acetyl, propionyl, etc.), mercapto, and $C_{1-6}$ alkylmercapto (e.g. methylmercapto, ethylmercapto, propylmercapto, etc.).

These substituent groups may be present in any substitutable positions and may number 1 to 3. When the number of substituents is not less than 2, such substituents may be similar or dissimilar.

The "6-membered hydrocarbon ring" of the "optionally substituted 6-membered hydrocarbon ring", represented by Ring B, includes but is not limited to benzene ring, cyclohexene ring and cyclohexane ring. Preferred are benzene and cyclohexene rings. Among the cyclohexene rings, preferred is a cyclohexene ring having a double bond which connects two bridge heads.

The substituent that may be present on the "6-membered hydrocarbon ring" includes but is not limited to the same substituent groups as mentioned for the "optionally substituted benzene ring". Preferred, among such substituent groups, are $C_{1-6}$ alkyl, $C_{1-6}$ alkoxy, nitro, and halogen. These substituent groups may be present in any substitutable positions and may number 1 to 3. When the number of substituents is not less than 2, such substituents may be similar or dissimilar.

The "lower alkylene group" represented by X includes but is not limited to $C_{1-6}$ alkylene group (e.g. methylene, ethylene, trimethylene, propylene, tetramethylene, etc.). Among others, preferred is ethylene.

The "lower alkyleneoxy group" represented by Y includes but is not limited to $C_{1-6}$ alkyleneoxy group (e.g. methyleneoxy, ethyleneoxy, trimethyleneoxy, propyleneoxy, tetramethyleneoxy, etc.). Among others, preferred is methyleneoxy.

The "alkyl" of the "alkyl" represented by $R^1$ and of the "alkyl group optionally substituted by an optionally substituted aromatic group", represented by R, includes but is not limited to $C_{1-6}$ alkyl (e.g. methyl, ethyl, propyl, isopropyl, butyl, isobutyl, sec-butyl, tert-butyl, pentyl, hexyl, etc.). Preferred are $C_{1-3}$ alkyl (e.g. methyl, ethyl, propyl, isopropyl, etc.).

The "aromatic group" for the "optionally substituted aromatic group" and the "alkyl group optionally substituted by an optionally substituted aromatic group", represented by R, can be an aromatic hydrocarbon group, a heteroaromatic group, or the like.

The "aromatic hydrocarbon group" mentioned above includes but is not limited to monocyclic and condensed polycyclic aromatic hydrocarbon groups each containing 6 to 14 carbon atoms. Typically, $C_{6-14}$ aryl groups such as phenyl, 1-naphthyl, 2-naphthyl, indenyl, anthryl, etc. can be mentioned. Preferred, among them, are phenyl, 1-naphthyl and 2-naphthyl. Phenyl is most preferred.

The "heteroaromatic group" mentioned above includes but is not limited to 5- to 10-membered heteroaromatic groups containing, besides carbon atoms, 1 to 4 hetero atoms of one or two species selected from among nitrogen, oxygen and sulfur. Among others, preferred is 5- or 6-membered monocyclic group. This group may be fused to one or two aromatic rings, such as benzene ring, pyridine ring, etc., to form a bicyclic or tricyclic condensed ring system. Thus, for example, 5- or 6-membered monocyclic heteroaromatic groups (e.g. 2- or 3-thienyl, 2- or 3-furyl, 2- or 3-pyrrolyl, 2-, 4- or 5-imidazolyl, 4- or 5-pyrazolyl, 3-, 4- or 5-isothiazolyl, 3-, 4- or 5-isoxazolyl, 2-, 3- or 4-pyridyl, 2-, 4- or 5-pyrimidinyl, 3- or 4-pyridazinyl, pyrazinyl, etc.) and bicyclic or tricyclic condensed ring systems formed on condensation of any of the heterocyclic groups with not less than one benzene ring (e.g. benzofuryl, benzothiazolyl, benzoxazolyl, benzimidazolyl, 1-indolyl, 2- or 3-quinolyl, 1- or 3-isoquinolyl, etc.) can be mentioned. Preferred are 5- or 6-membered monocyclic heteroaromatic groups each containing 1 to 3 hetero atoms selected from among nitrogen, oxygen and sulfur in addition to carbon as ring members (e.g. 2- or 3-thienyl, 2- or 3-furyl, 2-, 4- or 5-imidazolyl, 2-, 3- or 4-pyridyl, etc.) and bicyclic condensed ring systems (e.g. 1-indolyl, etc.) formed on condensation of such heterocyclic group as mentioned above with one benzene ring. Still more preferred is 2-, 3- or 4-pyridyl. The most preferred of them is 4-pyridyl.

The substituent group that may be present on the "aromatic group" includes groups similar to the substituent groups mentioned for the "optionally substituted benzene ring" as well as $C_{6-10}$ aryl (e.g. phenyl, etc.) and oxo. These substituent groups may be present in any substitutable positions of the aromatic group and may number 1 to 5, preferably 1 to 3. When the number of substituents is not less than 2, such substituents may be similar or dissimilar. Preferred substituents are halogen and $C_{1-6}$ alkoxy.

The "optionally substituted aromatic group" includes but is not limited to (i) a $C_{6-14}$ aryl group and (ii) a 5- to 10-membered heteroaromatic group containing, besides carbon atoms, 1 to 4 hetero atoms selected from among nitrogen, oxygen and sulfur, each of which group may have 1 to 5 substituents selected from among amino, mono-$C_{1-6}$ alkylamino, di-$C_{1-6}$ alkylamino, halogen, nitro, sulfo, cyano, hydroxy, $C_{1-6}$ alkyl, $C_{1-6}$ alkoxy, carboxy, $C_{1-6}$ alkoxycarbonyl, $C_{1-5}$ acyl, mercapto, $C_{1-6}$ alkylmercapto, $C_{6-10}$ aryl and oxo.

Referring to formula (I), Ring A is preferably an unsubstituted benzene ring.

Ring B is preferably an unsubstituted 6-membered hydrocarbon ring. More preferred is an unsubstituted benzene ring or an unsubstituted cyclohexene ring. The most preferred is an unsubstituted benzene ring.

X is preferably carbonyl.

Y is preferably an oxygen atom or >N—$R^1$ ($R^1$ is H or alkyl).

$R^1$ is preferably H or $C_{1-3}$ alkyl. Particularly preferred is H or methyl.

Y is more preferably >NH.

R is preferably an optionally substituted aromatic group or an alkyl group optionally substituted by an optionally substituted aromatic group. Particularly preferred is alkyl substituted by an optionally substituted aromatic group.

R is more preferably (1) (i) phenyl, (ii) naphthyl or (iii) pyridyl, each of which may have 1 to 5 substituents selected from among amino, mono-$C_{1-6}$ alkylamino, di-$C_{1-6}$ alkylamino, halogen, nitro, sulfo, cyano, hydroxy, $C_{1-6}$ alkyl, $C_{1-6}$ alkoxy, carboxy, $C_{1-6}$ alkoxycarbonyl, $C_{1-5}$ acyl, mercapto, $C_{1-6}$ alkylmercapto, $C_{6-10}$ aryl and oxo; or (2) $C_{1-3}$ alkyl optionally substituted by (i) phenyl or (ii) pyridyl, each of which may have 1 to 5 substituents selected from among amino, mono-$C_{1-6}$ alkylamino, di-$C_{1-6}$ alkylamino, halogen, nitro, sulfo, cyano, hydroxy, $C_{1-6}$ alkyl, $C_{1-6}$ alkoxy, carboxy, $C_{1-6}$ alkoxycarbonyl, $C_{1-5}$ acyl, mercapto, $C_{1-6}$ alkylmercapto, $C_{6-10}$ aryl and oxo.

Still more preferred is (1) (i) phenyl or (ii) naphthyl, which may be have 1 to 5 substituents selected from halogen and $C_{1-6}$ alkoxy or (2) $C_{1-3}$ alkyl optionally substituted by (i) phenyl or (ii) pyridyl, each of which may have 1 to 5 substituents selected from halogen and $C_{1-6}$ alkoxy.

The substituent group —NH—X—Y—R may be present in any substitutable positions on the benzene ring. The preferred position of substitution is the 3-position or the 4-position of the benzene ring. The 4-position is particularly preferred.

n is preferably equal to 1.

m is preferably equal to 1.

Preferred species of the compound of the invention includes those in which, referring to formula (I), Ring A is an unsubstituted benzene ring; Ring B is an unsubstituted benzene ring or an unsubstituted cyclohexene ring; X is methylene, carbonyl or sulfonyl; Y is a bond, oxygen, methyleneoxy or a group of the formula: >N—$R^1$; $R^1$ is hydrogen or $C_{1-3}$ alkyl; R is (1) (i) phenyl, (ii) naphthyl or (iii) pyridyl, each of which may have 1 to 5 substituents selected from among amino, mono-$C_{1-6}$ alkylamino, di-$C_{1-6}$ alkylamino, halogen, nitro, sulfo, cyano, hydroxy, $C_{1-6}$ alkyl, $C_{1-6}$ alkoxy, carboxy, $C_{1-6}$ alkoxycarbonyl, $C_{1-5}$ acyl, mercapto, $C_{1-6}$ alkylmercapto, $C_{6-10}$ aryl and oxo or (2) $C_{1-3}$ alkyl optionally substituted by (i) phenyl or (ii) pyridyl, each of which may have 1 to 5 substituents selected from among amino, mono-$C_{1-6}$ alkylamino, di-$C_{1-6}$ alkylamino, halogen, nitro, sulfo, cyano, hydroxy, $C_{1-6}$ alkyl, $C_{1-6}$ alkoxy, carboxy, $C_{1-6}$ alkoxycarbonyl, $C_{1-5}$ acyl, mercapto, $C_{1-6}$ alkylmercapto, $C_{6-10}$ aryl and oxo; n is 1; and m is 1.

Still more preferred are compounds in which, referring to formula (I), Ring A is an unsubstituted benzene ring; Ring B is an unsubstituted benzene ring; X is carbonyl; Y is >NH; R is $C_{1-3}$ alkyl substituted by (i) phenyl or (ii) pyridyl, each of which may be substituted by halogen or $C_{1-6}$ alkoxy; n is 1; and m is 1.

The following is a partial list of preferred compounds and salts of the invention.

(1) (3aR*,10aS*)-9-[4-(Benzyloxycarbonylamino)benzyl]-4-(2H-1,3-dioxo-1,3,4,5,6,7-hexahydroisoindole-2-acetyl)-2,3,3a,4,9,10a-hexahydrobenzo[b]cyclopenta[e][1,4]diazepin-10(1H)-one (2) (3aR*,10aS*)-9-[4-(3-Benzylureido)benzyl]-4-(phthalimidoacetyl)-2,3,3a,4,9,10a-hexahydrobenzo[b]cyclopenta[e][1,4]diazepin-10(1H)-one (3) (3aR*,10aS*)-9-[4-(3-Benzylureido)benzyl]-4-(2H-1,3-dioxo-1,3,4,5,6,7-hexahydroisoindole-2-acetyl)-2,3,3a,4,9,10a-hexahydrobenzo[b]cyclopenta[e][1,4]diazepin-10(1H)-one (4) (3aR*,10aS*)-9-[4-[3-((R)-1-Phenylethyl)ureido]benzyl]-4-(phthalimidoacetyl)-2,3,3a,4,9,10a-hexahydrobenzo[b]cyclopenta[e][1,4]diazepin-10(1H)-one (5) (3aR*,10aS*)-9-[4-[3-(2-Phenylethyl)ureido]benzyl]-4-(phthalimidoacetyl)-2,3,3a,4,9,10a-hexahydrobenzo[b]-cyclopenta[e][1,4]diazepin-10(1H)-one (6) (3aR*,10aS*)-9-[4-[3-(4-Fluorobenzyl)ureido]benzyl]-4-(phthalimidoacetyl)-2,3,3a,4,9,10a-hexahydrobenzo[b]-cyclopenta[e][1,4]diazepin-10(1H)-one (7) (3aR*,10aS*)-9-[4-[3-(4-Methoxybenzyl)ureido]-benzyl]-4-(phthalimidoacetyl)-2,3,3a,4,9,10a-hexahydrobenzo[b]cyclopenta[e][1,4]diazepin-10 (1H)-one (8) (3aR*,10aS*)-4-(Phthalimidoacetyl)-9-[4-[3-(4-pyridylmethyl)ureido]benzyl]-2,3,3a,4,9,10a-hexahydrobenzo[b]cyclopenta[e][1,4]diazepin-10 (1H)-one hydrochloride The salt of compound (I) according to the present invention is preferably a medicinally acceptable acid addition salt or base addition salt. Thus, the salt of compound (I) includes but is not limited to salts with inorganic acids such as hydrochloric acid, hydrobromic acid, hydroiodic acid, sulfuric acid, phosphoric acid, etc., salts with organic acids such as acetic acid, oxalic acid, succinic acid, ascorbic acid, maleic acid, lactic acid, citric acid, tartaric acid, methanesulfonic acid, benzoic acid, benzenesulfonic acid, etc., salts with inorganic bases such as alkali metals, e.g. sodium, potassium, etc., or alkaline earth metals, e.g. calcium, magnesium, etc., ammonium salts, and salts with organic bases such as organic amines, e.g. methylamine, ethylamine, propylamine, isopropylamine, butylamine, tert-butylamine, dimethylamine, diethylamine, trimethylamine, triethylamine, pyridine, picoline, dicyclohexylamine, N,N'-dibenzylethylenediamine, etc., and salts with basic amino acids such as lysine, arginine and so on.

While there exist optical isomers depending on species of the compound of the invention, such optical isomers are also subsumed in the category of the compound of the invention.

Optical isomers can be obtained by the per se known technology. Thus, such isomers can be selectively produced by using optically active synthetic intermediates or subjecting racemic compounds to optical resolution in the conventional manner.

The optical resolution technology includes a method which comprises producing a salt with an optically active acid and separating the salt by fractional crystallization, a method which comprises subjecting a racemic compound or salt to chromatographic fractionation using a chiral column, e.g. ENANTIO-OVM (Tohso Corporation), and a suitable developer such as water, buffers (e.g. phosphate buffer), organic solvents [alcohols (e.g. methanol, ethanol, etc.), nitriles (e.g. acetonitrile), hexane, diethyl ether, etc.] and mixtures of such solvents, and a method which comprises condensing a racemic mixture with an optically active organic acid, such as α-methoxy-α-(trifluoromethyl)phenylacetic acid (MTPA), menthoxyacetic acid or the like, in the conventional manner, typically by the acid chloride method, to give a mixture of amide diastereomers, then subjecting it to a fractionation procedure such as fractional recrystallization or silica gel column chromatography, and finally subjecting the corresponding amide to acidic hydrolysis or basic hydrolysis.

While the compound (I) and salt of the invention can be produced by various processes known per se, the following processes can be mentioned as typical examples.

The compound (I) of the invention can be typically synthesized according to Reaction Schema-1 to Reaction Schema-4, inclusive of their modifications. All the compounds (Ia) through (Ie) indicated in these reaction schemes fall within the scope of the compound (I) of the invention.

REACTION SCHEMES

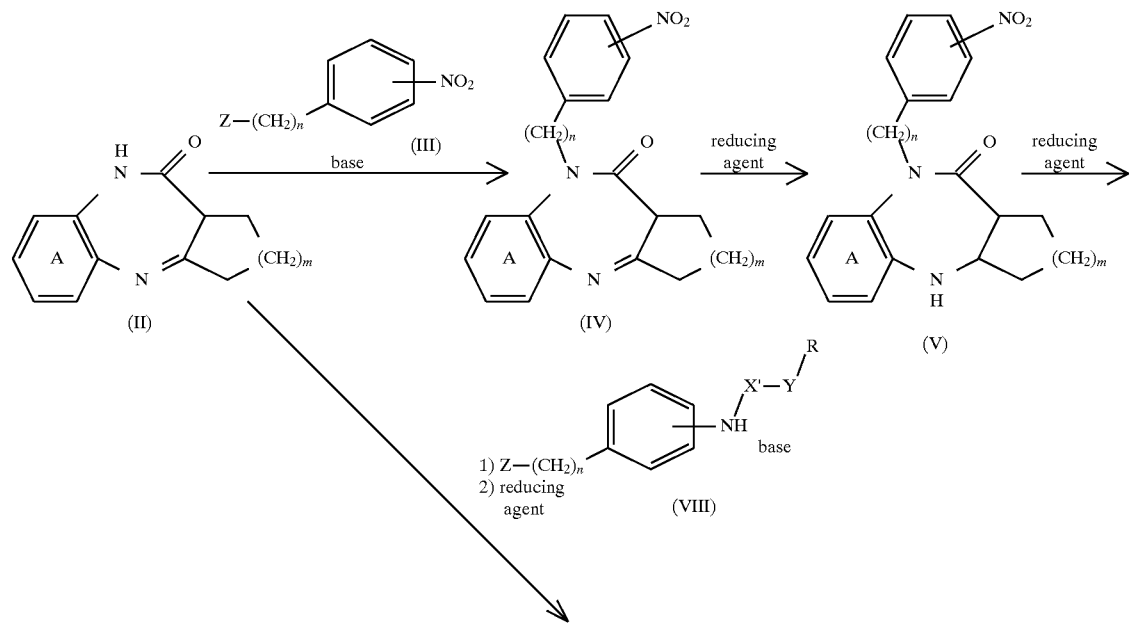

-continued
Reaction Schema-1
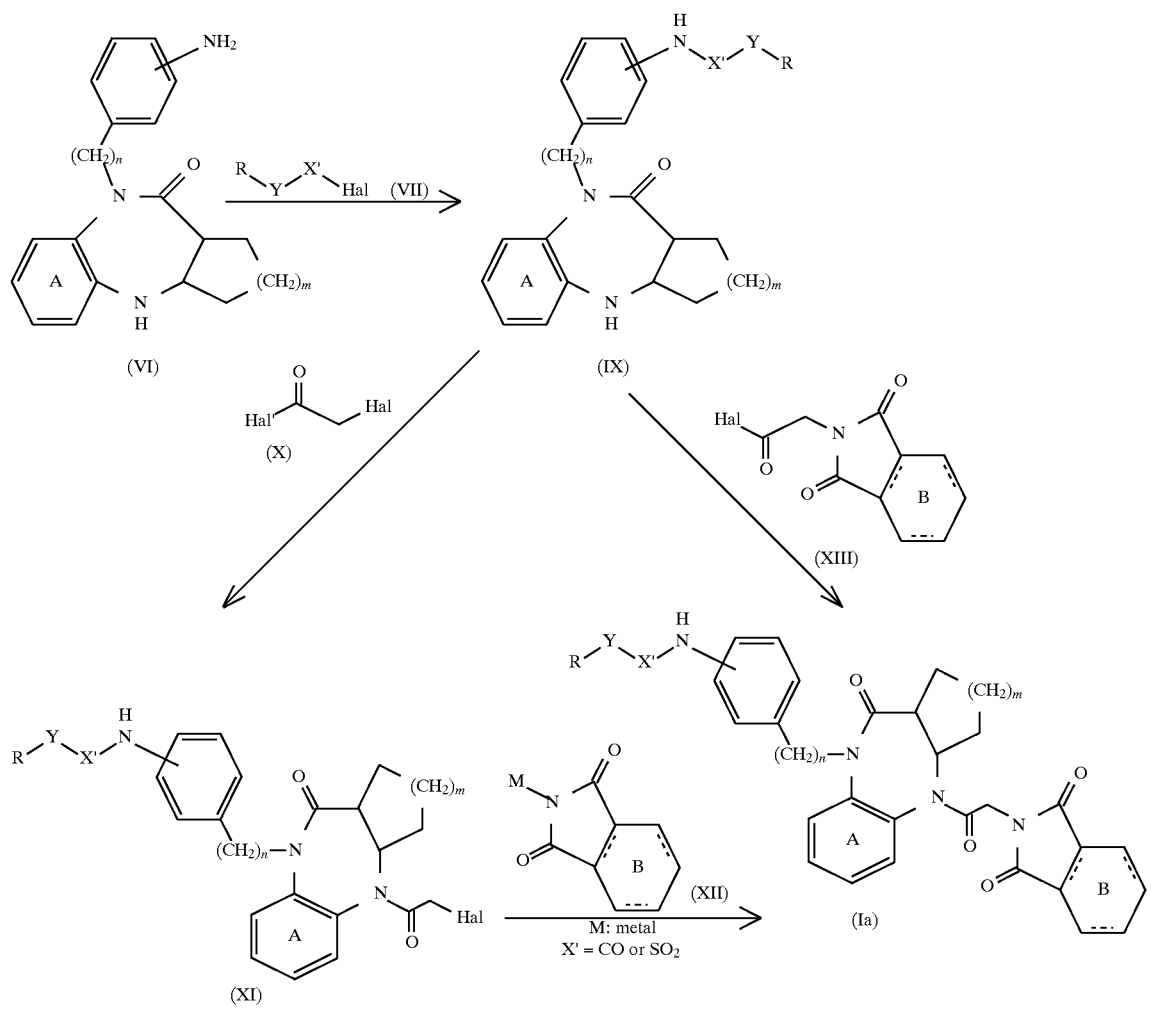
Hal: halogen
Hal': halogen
Z: leaving group (e.g. halogen, alkyl sulfonate
    aryl sulfonate, etc.)
Reaction Schema-2
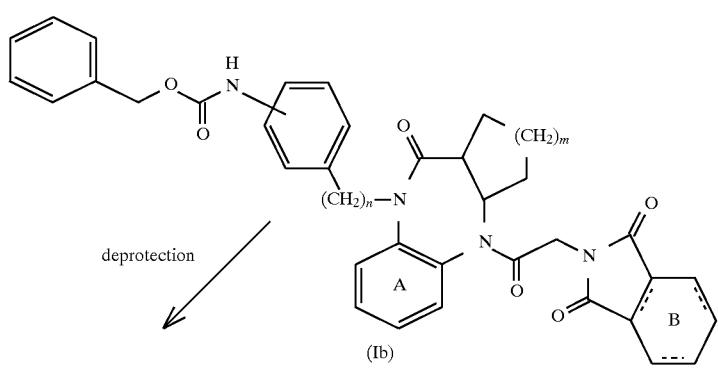

-continued
Reaction Schema-2
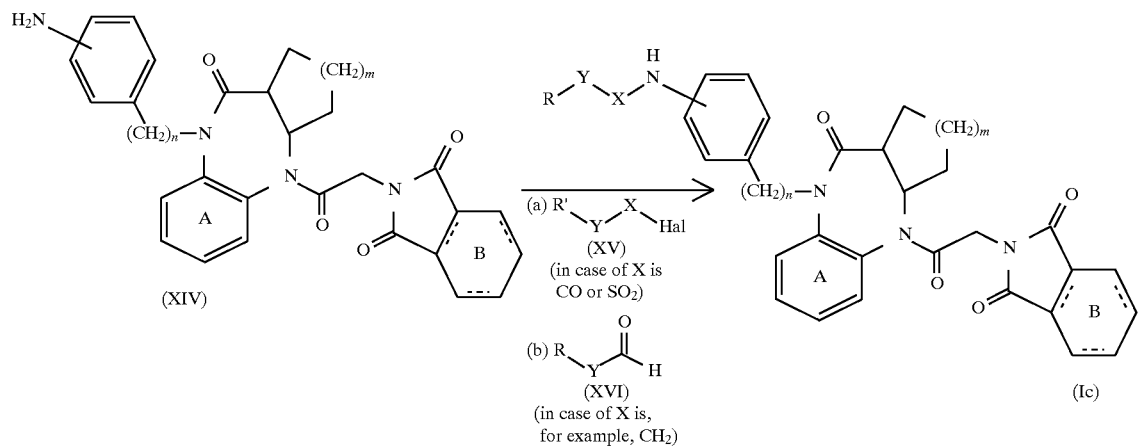
Reaction Schema-3
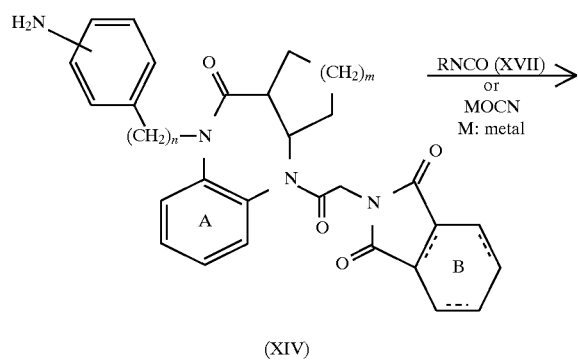
-continued
Reaction Schema-3
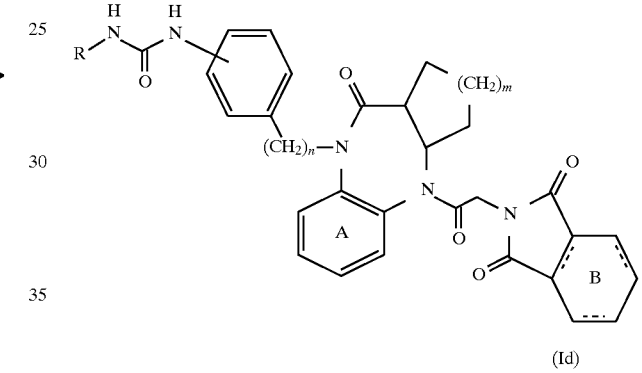
Reaction Schema-4
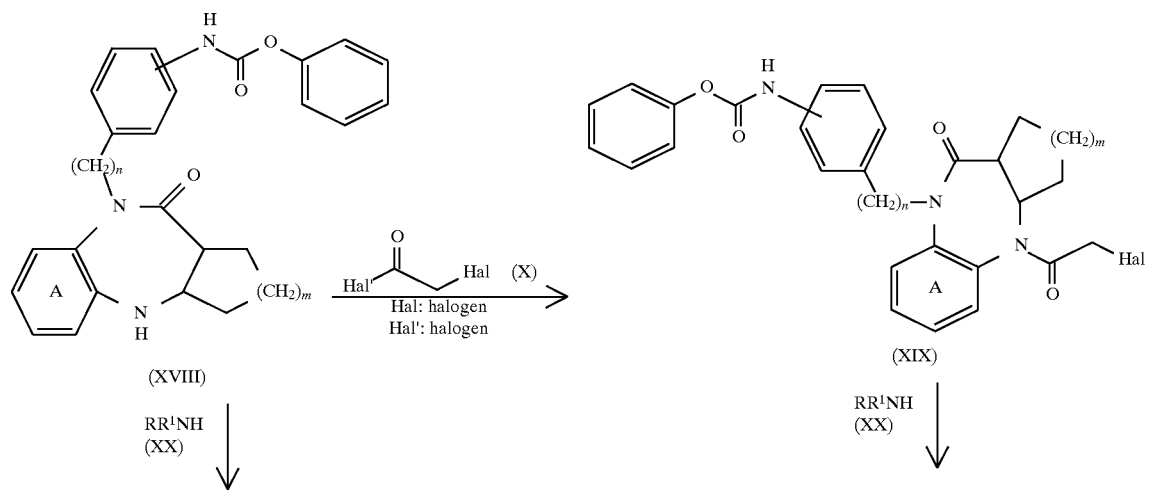

-continued
Reaction Schema-4

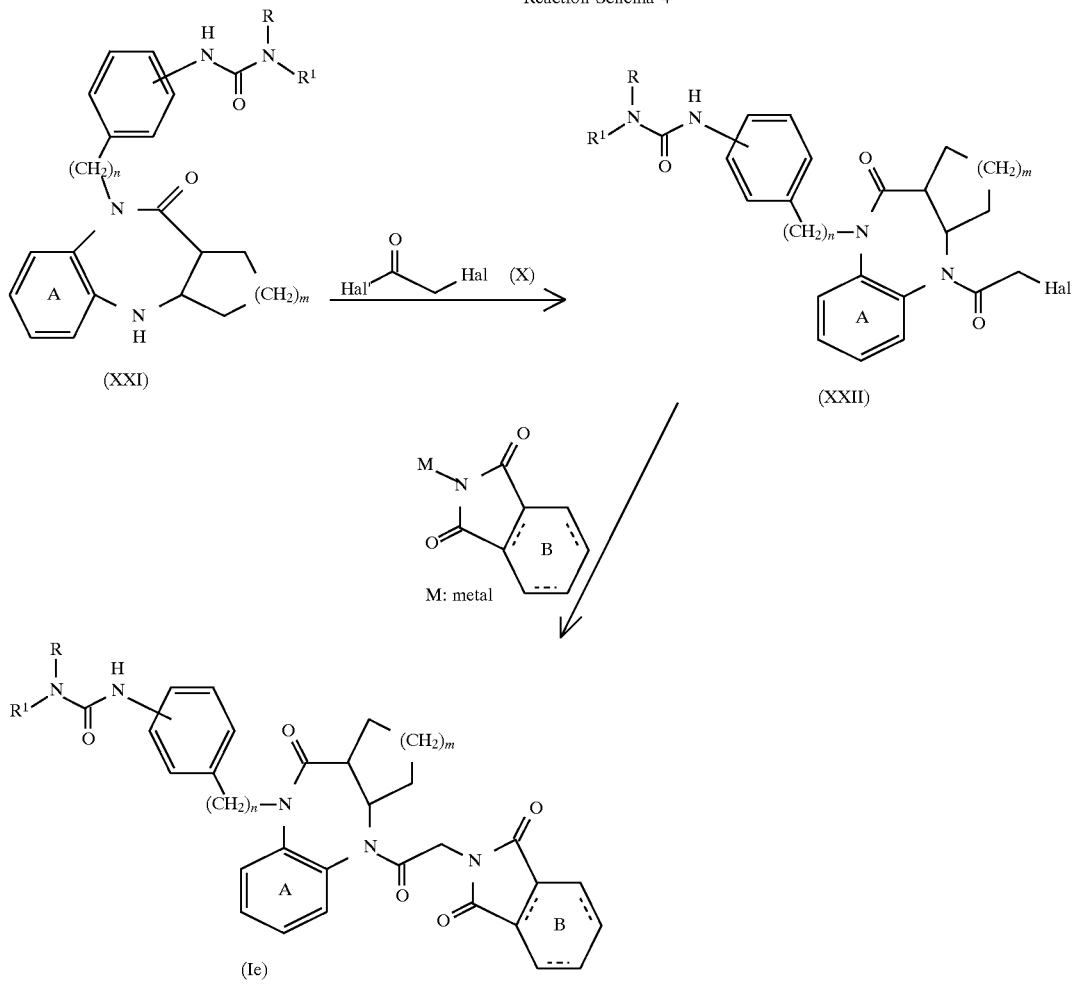

The reaction procedures according to Reaction Schema-1 to Reaction Schema-4 are now described in detail.

In the practice of the present invention, compound (Ia) can be produced by subjecting compound (IX) and compound (XIII) to condensation reaction. This condensation between compound (IX) and compound (XIII) can be carried out in the absence of a solvent or in the presence of an inert solvent. The inert solvent that can be used typically includes halogenated hydrocarbons such as dichloroethane, chloroform, etc., aliphatic hydrocarbons such as hexane, cyclohexane, etc., aromatic hydrocarbons such as toluene, xylene, etc., ethers such as diethyl ether, diisopropyl ether, etc., amides such as N,N-dimethylformamide, N,N-dimethylacetamide, etc., and various mixtures of such solvents. This condensation reaction can be carried out in the presence of a base. The base that can be used for this purpose includes but is not limited to triethylamine, sodium hydride, sodium alkoxides, sodium hydroxide, and potassium carbonate. The solvent is used in a proportion of generally 0.2–50 milliliters and preferably 3–20 mL per gram of compound (IX). This reaction is carried out usually at −5° to 200° C. and preferably at 5° to 150° C. The reaction time is generally about 5 minutes to about 120 hours and preferably about 15 min. to 90 hr. Compound (XIII) is a known compound and can be typically synthesized by the process described in EP 539977A1.

Compound (Ia) can also be synthesized by subjecting compound (XI) and compound (XII) to condensation reaction. Compound (XII) for use in this condensation reaction is a known compound and can be either purchased from a commercial source or domestically produced by reacting the corresponding imide with a metal hydride (e.g. sodium hydride, potassium hydride, etc.), metal amide (e.g. lithium diisopropylamide, lithium hexamethyldisilazide, etc.) or metal alkoxide (e.g. sodium methoxide, sodium ethoxide, potassium tert-butoxide, etc.) in the conventional manner. The solvent and other reaction parameters can be similar to those mentioned for the condensation reaction between compound (IX) and compound (XIII).

Compound (XI) can be synthesized by reacting compound (IX) with haloacetyl halide (X). This condensation reaction can be conducted in the absence of a solvent or in the presence of an inert solvent. The inert solvent that can be used includes halogenated hydrocarbons such as dichloroethane, chloroform, etc., aliphatic hydrocarbons such as hexane, cyclohexane, etc., aromatic hydrocarbons such as toluene, xylene, etc., ethers such as diethyl ether, diisopropyl ether, etc., amides such as N,N-dimethylformamide, N,N-dimethylacetamide, etc., water, and mixtures of such solvents. This condensation reaction can be conducted in the presence of a base. The base that can be used includes but is not limited to triethylamine, sodium hydride, sodium alkoxides, sodium hydroxide, potassium carbonate and sodium carbonate. The solvent is used in a proportion of generally 0.2 to 300 mL and preferably 5 to 150 mL per gram of compound (IX). This reaction is conducted generally at −5° C. to 200° C., preferably 5° to 150° C. The reaction time is generally about 5 minutes to about 72 hours and preferably about 10 min. to about 10 hr. The haloacetyl halide (X) is a known compound and can be either purchased from a commercial source or domestically produced by reacting the corresponding halocarboxylic acid with a halogenating agent (e.g. thionyl chloride, phosphorus oxychloride, etc.).

Compound (IX) can be synthesized by subjecting compound (VI) and compound (VII) to condensation reaction. The parameters of this condensation reaction can be similar to those described for the condensation of compounds (IX) and (XIII). Compound (VII), as a class, is a known compound and any of carbobenzoxy chloride, carboxylic acid chlorides, sulfonic acid chlorides, etc. can be utilized.

Compound (VI) can be produced by reducing the nitro group of compound (V) either by reduction with a reducing agent or by catalytic reduction. The reducing agent that can be employed includes metal hydride complex compounds (e.g. lithium aluminum hydride, sodium borohydride, etc.), metals (zinc, tin, iron, etc.) and metal halides (e.g. stannous chloride etc.). The catalyst for catalytic reduction includes platinum oxide, palladium-on-carbon, Raney nickel and so on. Reduction with sodium borohydride is carried out typically in an alcoholic solvent, e.g. methanol, ethanol, etc., or a mixture of such an alcoholic solvent with an inert organic solvent (e.g. diethyl ether, tetrahydrofuran, etc.). Reduction with lithium aluminum hydride is carried out generally in an ether, e.g. diethyl ether, tetrahydrofuran, etc., or a mixture of such an ether with an inert solvent (e.g. hexane, cyclohexane, etc.). The proportion of the solvent is generally 0.2 to 50 mL and preferably 5 to 20 mL per gram of compound (V). The amount of the reducing agent is generally 1 to 3 equivalents and preferably 1 to 1.5 equivalents. The reaction temperature is −20° C. to 60° C., preferably 0° to 20° C. Reduction with a metal is generally carried out in acidic solution (hydrochloric acid, acetic acid, etc.) but when zinc is employed, the reaction can also be conduced under neutral to basic conditions. The amount of the metal is generally 3 equivalents to a large excess. The reaction temperature is −20° C. to 150° C., preferably 15° to 100° C. Reduction with a metal halide is generally carried out using an alcoholic (e.g. methanolic or ethanolic) solution acidic to hydrochloric acid or acetic acid. The proportion of the solvent is generally 0.2 to 50 mL and preferably 5 to 20 mL per gram of compound (V). The amount of the metal halide is generally 3 to 10 equivalents. The reaction temperature is −20° C. to 100° C., preferably 0° to 60° C.

The solvent that can be used for catalytic reduction includes alcohols such as methanol, ethanol, etc., carboxylic acids such as acetic acid etc., ethers such as diethyl ether, tetrahydrofuran, etc., and mixtures of such solvents. The proportion of the solvent is generally 0.2 to 50 mL and preferably 5 to 20 mL per gram of compound (V). The amount of the catalyst is generally 5 to 30% equivalent by weight. The reaction temperature is 0° to 80° C., preferably 20 to 60° C.

Compound (V) can be produced typically by reducing compound (IV) with a metal hydride complex compound. The metal hydride complex compound that can be used includes sodium cyanoborohydride and sodium borohydride. The solvent includes alcohols, such as methanol, ethanol, etc., and mixtures of such alcohols with other inert organic solvents (e.g. diethyl ether, tetrahydrofuran, etc.). For pH adjustment, a protic acid such as hydrochloric acid is employed. The amount of the reducing agent is generally 1–3 equivalents and preferably 1–1.5 equivalents. The proportion of the solvent is generally 0.2 to 50 mL and preferably 5 to 20 mL per gram of compound (IV). The reaction temperature is −20° C. to 60° C., preferably 0° to 20° C. The reaction time is generally 5 minutes to 5 hours and preferably 10 min. to 1 hr.

Compound (IV) can be synthesized by the per se known technology, typically by the reaction between compound (II) and compound (III) as described in J. Org. Chem. USSR, 1978, 14, 286. The conditions of this condensation reaction can be similar to those described for the condensation of compounds (IX) and (X).

Compound (IX) can also be produced by reacting compound (II) with compound (VIII). This reaction can be carried out in two steps. The conditions of the first-step reaction are similar to those of the condensation reaction of compounds (IX) and (XIII) and the conditions of the second-step reaction are similar to those used for the synthesis of compound (V). Compound (VIII) can be synthesized by N-acylating the corresponding aminophenylalkanol in the conventional manner and, then, sulfonylating or halogenating the N-acyl compound in the conventional manner.

In the practice of the present invention, compound (Ic) can be synthesized by subjecting compound (XIV) and compound (XV) to condensation reaction. The conditions of condensation are similar to those described for the condensation reaction between compound (IX) and compound (X).

Compound (Ic) can also be synthesized by reductive condensation reaction between compound (XIV) and compound (XVI). This condensation reaction is carried out in a solvent indifferent to the reaction, typically acetic acid or alcohol (e.g. ethanol, methanol, etc.) or a mixture of such a solvent with an ordinary inert solvent (e.g. halogenated hydrocarbons such as chloroform etc. and ethers such as diethyl ether, tetrahydrofuran, etc.). The adduct obtained is then reduced with a hydride-series reducing agent, preferably a mild reducing agent such as sodium triacetoxyborohydride [$Na(OAc)_3BH$] or sodium cyanoborohydride, optionally in the presence of a protic acid such as hydrochloric acid. The proportion of the solvent is generally 0.2 to 50 mL and preferably 5 to 25 mL per gram of compound (XIV). The reaction temperature need not be critically controlled but the preferred range is usually about 0° to 100° C. The reaction time is about 5 minutes to about 10 hours, preferably 10 min. to 3 hr.

Compound (XIV) can be synthesized by removing the amino-protecting group from compound (Ib). This deprotection reaction can be carried out by the per se known procedures, such as hydrolysis with an acidic or basic catalyst, solvolysis, amine exchange reaction, reduction with a reducing agent, or catalytic reduction. The solvent that can be used for such hydrolysis or solvolysis includes water, alcohols (e.g. methanol, ethanol, etc.), acetic acid, and mixtures of any such solvent with other inert organic solvents (e.g. tetrahydrofuran, chloroform, dimethyl sulfoxide, etc.). The proportion of the solvent is generally 0.2 to 50 mL and preferably 5 to 20 mL per gram of compound (Ib). The acid that can be used for hydrolysis includes but is not limited to hydrochloric acid, sulfuric acid, hydrobromic acid, acetic acid and trifluoroacetic acid, and the base that can be used includes but is not limited to sodium hydroxide, potassium hydroxide, potassium carbonate and aqueous ammonia. The proportion of the acid or the base is generally 0.1 to 30 equivalents based on compound (Ib).

The amine that can be used for the amine exchange reaction includes but is not limited to methylamine, ethylamine, and ammonia and its amount relative to compound (Ib) is generally 1 to 30 equivalents. The solvent can be any organic solvent indifferent to the reaction and its proportion is generally 0.2 to 50 mL and preferably 5 to 20 mL per gram of compound (Ib).

The reducing agent includes but is not limited to lithium aluminum hydride, sodium borohydride and sodium cyanoborohydride, and its amount relative to compound (Ib) is generally 1 to 10 equivalents. The solvent that can be used for the reduction with lithium aluminum hydride may for example be an ether, e.g. tetrahydrofuran, diethyl ether, etc., and the solvent for the reduction with sodium borohydride or sodium cyanoborohydride may for example be an alcohol (e.g. methanol, ethanol, etc.) or a mixture of such alcohol with an inert solvent (e.g. hexane, chloroform, ethers, etc.). The solvent is used in a proportion of generally 0.2 to 50 mL and preferably 5 to 20 mL per gram of compound (Ib).

The solvent that can be used for catalytic reduction includes but is not limited to alcohols, e.g. methanol, ethanol, etc., carboxylic acids, e.g. acetic acid etc., ethers, e.g. diethyl ether, tetrahydrofuran, etc., and mixtures of such solvents. The proportion of the solvent is generally 0.2 to 50 mL and preferably 5 to 20 mL per gram of compound (Ib). The catalyst for use in this reaction includes palladium-on-carbon, platinum oxide, and Raney nickel to mention just a few. The amount of the catalyst is 5 to 30% equivalent by weight. The reaction temperature is not critical but is generally 0° to 80° C. and preferably 20° to 60° C.

Compound (Ib) is subsumed in the category of the compound (Ia) and can be synthesized in accordance with Reaction Schema-1 presented hereinbefore.

Compound (Id) can be synthesized by reacting compound (XIV) with compound (XVII). The solvent for this condensation reaction can be any inert solvent and generally includes aromatic hydrocarbons such as benzene, toluene, etc., halogenated hydrocarbons such as chloroform, dichloromethane, etc., ethers such as tetrahydrofuran, diethyl ether, etc., and acetone. The proportion of the solvent is generally 0.2 to 50 mL and preferably 5 to 30 mL per gram of compound (XIV). While the reaction temperature is not so critical, the reaction is generally conducted at −5° C. to 120° C. The reaction time is generally 10 minutes to 10 hours.

Compound (Id) can be synthesized using sodium cyanate, potassium cyanate or the like in lieu of compound (XVII). In this case, based on compound (XIV), about 1 to 5 equivalents of sodium cyanate or potassium cyanate and about 1 to 30 equivalents of an acid (e.g. acetic acid, trifluoroacetic acid, hydrochloric acid, etc.) are used. The solvent for this condensation reaction can be any solvent that is indifferent to the reaction. Thus, aromatic solvents such as benzene, toluene, etc., halogenated hydrocarbons such as chloroform, dichloromethane, etc., ethers such as tetrahydrofuran, diethyl ether, etc., and acetone can be used generally as the solvent. The proportion of the solvent is generally 0.2 to 50 mL and preferably 5 to 20 mL per gram of compound (Ib).

In the practice of the present invention, compound (Ie) can be synthesized by subjecting compound (XXII) and compound (XII) to condensation reaction. The conditions of this condensation reaction can be similar to those for the condensation of compounds (XI) and (XII).

Compound (XXII) can be synthesized by subjecting compound (XXI) and compound (X) to condensation reaction. The conditions of this condensation reaction can be similar to those for the condensation of compounds (IX) and (X).

Compound (XXI) can be synthesized by reacting compound (XVIII) with compound (XX). The solvent for this condensation reaction can be any solvent that is indifferent to the reaction. Thus, for example, aromatic solvents such as benzene, toluene, etc. halogenated hydrocarbons such as chloroform, dichloromethane, etc., ethers such as tetrahydrofuran, diethyl ether, etc., and amides such as N,N-dimethylformamide can be employed. The solvent is used in a proportion of generally 0.2 to 50 mL and preferably 5 to 20 mL per gram of compound (XVII). The reaction time is generally 5 minutes to 120 hours and preferably 15 min. to 90 hr.

Compound (XXII) can also be synthesized by reacting compound (XVIII) with compound (X) and, then, reacting the resulting compound (XIX) with compound (XX). The conditions of these reactions can be similar to those described above.

Compound (XVIII) is subsumed in the category of the compound (IX) and can be synthesized by the procedure mentioned for the synthesis of compound (IX) in Reaction Schema-1.

In case any of the above-mentioned compounds is capable of forming a salt, the salt can likewise be used in the contemplated reaction. In such cases, the amount of the base and/or other reactant should of course be increased to compensate for the amount that will be consumed for neutralization of the ion. The above salts of the compounds includes but is not limited to salts with inorganic acids such as hydrochloric acid, hydrobromic acid, hydroiodic acid, sulfuric acid, phosphoric acid, etc., salts with organic acids such as acetic acid, oxalic acid, succinic acid, ascorbic acid, maleic acid, lactic acid, citric acid, tartaric acid, methanesulfonic acid, benzoic acid, benzenesulfonic acid, etc., salts with inorganic bases such as alkali metals, e.g. sodium, potassium, etc., or alkaline earth metals, e.g. calcium, magnesium, etc., ammonium salts, and salts with organic bases such as organic amines, e.g. methylamine, ethylamine, propylamine, isopropylamine, butylamine, tert-butylamine, dimethylamine, diethylamine, trimethylamine, triethylamine, pyridine, picoline, dicyclohexylamine, N,N'-dibenzyl-ethylenediamine, etc., and salts with basic amino acids such as lysine, arginine and so on.

Compound (I) can also be synthesized by utilizing one or more of the per se known deprotection reaction, acylation reaction, alkylation reaction, hydrogenation reaction, oxidation reaction, reduction reaction, carbon chain extending reaction and substituent group exchange reaction in the above-described reaction steps. These reactions can be conducted typically according to the procedures described in Shin Jikken Kagaku Koza [New Lectures on Experimental Chemistry], Vol. 14 and Vol. 15 [ed. by The Chemical Society of Japan, 1977–78].

Where any functional group has to be protected in conducting the reactions described above, the introduction and elimination of protective groups can be carried out by the known procedures, for example, Protective Groups in Organic Synthesis, 2nd Ed., 1991.

Where the objective compound obtained by any of the above reactions is a free compound, it can be converted to a salt in the convention manner. When the reaction product is a salt, it can be converted to the free compound or a different kind of salt also in the conventional manner.

The compound (I) or salt thus produced can be separated from the reaction mixture and purified by known procedures such as redistribution, concentration, solvent extraction, fractional distillation, crystallization, recrystallization, chromatography, and so on.

Where compound (I) exists as diastereomers, conformers or the like, they can be respectively isolated by the fractionation and purification procedures mentioned above. Moreover, where compoundd (I) is an optically active compound, it can be resolved into d-and l-isomers by the conventional optical resolution technology.

Having excellent GnRH receptor antagonizing activity, the compound (I), inclusive of its salt, of the present invention inhibits secretion of gonadotrophic hormones to keep blood steroid hormone levels low. Therefore, it can be used with advantage as an ovulation inhibitor, an ovulation inducing agent, a contraceptive, or an implantation inhibitor in man and other mammals (e.g. mouse, rat, rabbit, dog, bovine, swine, etc.) or as a prophylactic-therapeutic agent for amenorrhea, prostate cancer, prostatic hypertrophy, endometriosis, hysteromyoma, breast cancer, acne, precocious puberty, premenstrual syndrome, polycystic ovary syndrome, hyperandrogenism, etc. in man. Moreover, the compound (I) and salt can also be used for modulation of the estrous cycle and promotion of growth in animals, improving of meat quality, promotion of egg production in fish. Furthermore, the compound (I), inclusive of its salt, can be used in combination with a steroidal or non-steroidal anti-androgen. The compound (I), inclusive of its salt, of the invention features a low toxic potential and a low risk of side effect.

The compound (I) of this invention, inclusive of its salt, can be safely administered, either as it is or in the form of a pharmaceutical composition containing a medicinally acceptable carrier, either orally or by routes other than the peroral, in a variety of dosage forms such as tablets (inclusive of dragees, film-coated tablets, etc.), powders, granules, capsules (inclusive of soft capsules), elixirs, injections, suppositories, controlled-release preparations and other drug delivery systems. The dosage is dependent on the subject, administration route, type of disease, and other factors but taking oral administration to an adult patient with prostatic hypertrophy as an example, about 0.1 to about 20 mg/kg/dose, preferably about 0.5 to about 10 mg/kg/dose as active ingredient (compound (I) or a salt thereof) can be administered once or a few times daily.

The medicinally acceptable carrier mentioned above includes varieties of organic and inorganic materials conventionally used in pharmaceutical practice. These materials are used as excipients, lubricants, binders, disintegrators, etc. for solid dosage forms and solvents, solubilizers, suspending agents, isotonizing agents, buffers, soothing agents or local anesthetics, etc. for liquid dosage forms. Where necessary, such additives as preservatives, antioxidants, coloring agents, sweeteners or corrigents, etc. can also be incorporated. Preferred excipients are lactose, sucrose, D-mannitol, starch, crystalline cellulose, and light silicic anhydride, among others. Preferred lubricants are magnesium stearate, calcium stearate, talc, colloidal silica, and so on. Preferred binders are crystalline cellulose, sucrose, D-mannitol, dextrin, hydroxypropylcellulose, hydroxypropylmethylcellulose, polyvinylpyrrolidone, and so on. Preferred disintegrators are starch, carboxymethylcellulose, carboxymethylcellulose calcium, croscarmellose sodium, and carboxymethylstarch sodium, to name but a few. Preferred solvents are water for injection, alcohol, propylene glycol, macrogols, sesame oil, corn oil, etc. Preferred solubilizers are polyethylene glycol, propylene glycol, D-mannitol, benzyl benzoate, ethanol, trisaminomethane, cholesterol, triethanolamine, sodium carbonate, sodium citrate, and so on. Among preferred suspending agents are various surfactants such as stearyltriethanolamine, sodium lauryl sulfate, laurylaminopropionic acid, lecithin, benzalkonium chloride, benzethonium chloride, glyceryl monostearate, etc., and hydrophilic macromolecular substances such as polyvinyl alcohol, polyvinylpyrrolidone, carboxymethylcellulose sodium, methylcellulose, hydroxymethylcellulose, hydroxyethylcellulose, hydroxypropylcellulose, etc. Preferred isotonizing agents are sodium chloride, glycerol, D-mannitol, etc. Among preferred buffers are phosphate, acetate, carbonate, and citrate buffers. Benzyl alcohol can be mentioned as a typical preferred soothing agent. Preferred preservatives are p-hydroxybenzoic acid esters, chlorobutanol, benzyl alcohol, phenethyl alcohol, dehydroacetic acid, sorbic acid, etc. Among preferred antioxidants are salts of sulfurous acid, ascorbic acid, α-tocopherol, and so on.

BEST MODE FOR CARRYING OUT THE INVENTION

EXAMPLES

The following reference, working and experimental examples describe the present invention in further detail. However, these examples are given for purposes of illustration only and should by no means be construed as defining the scope of the invention. It should also be understood, therefore, that many changes and modifications can be made by those skilled in the art without departing from the scope of the claims.

The term "room temperature" as used in the following reference and working examples means a temperature within the range of 0°–30° C. The other symbols have the following meanings.

s: singlet
d: doublet
t: triplet
q: quartet
quint: quintet
sext: sextet
m: multiplet
br: broad
J: coupling constant
Hz: hertz
$CDCl_3$: deuterochloroform
THF: tetrahydrofuran
DMF: N,N-dimethylformamide
DMSO: dimethyl sulfoxide
$^1$H NMR: proton nuclear magnetic resonance

Reference Example 1

9-(4-Nitrobenzyl)-2,3,9,10a-tetrahydrobenzo[b]cyclopenta[e][1,4]diazepin-10(1H)-one A suspension of 2,3,9,10a-tetrahydrobenzo[b]-cyclopenta[e][1,4]diazepin-10(1H)-one (25.00 g, 0.125 mmol) in N,N-dimethylformamide (DMF) (150 mL) was cooled to 0° C. and sodium hydride (60% dispersion in liquid paraffin, 5.00 g, 0.125 mol) was added. The mixture was stirred at the same temperature for 10 minutes and then at 20° C. for 5 minutes. After the resulting solution was cooled to 0° C., 4-nitrobenzyl bromide (28.32 g, 0.131 mol) was added and the mixture was stirred at 20° C. for 10 minutes. This reaction mixture was poured in saturated aqueous ammonium chloride solution (500 mL) and the resulting precipitate was recovered by filtration, rinsed with water, and recrystallized from dichloromethane-ethanol to provide 29.76 g (yield 71%) of the title compound. Samples for analysis were recrystallized from chloroform-ethanol. m.p. 185°–188° C.

$^1$H NMR (CDCl$_3$) δ: 1.9–2.1 (3H, m), 2.6–2.8 (3H, m), 3.0–3.1 (1H, m), 5.12 (1H, d, J=16.0 Hz), 5.29 (1H, d, J=16.4 Hz), 7.1–7.4 (6H, m), 8.1–8.2 (2H, m).

Reference Example 2

9-(3-Nitrobenzyl)-2,3,9,10a-tetrahydrobenzo[b]cyclopenta[e][1,4]diazepin-10(1H)-one A solution of 2,3,9,10a-tetrahydrobenzo[b]cyclopenta[e][1,4]diazepin-10(1H)-one (4.00 g, 20 mmol) in DMF (40 mL) was cooled to 0° C. and sodium hydride (a 60% dispersion in liquid paraffin, 0.80 g, 20 mmol) was added. This mixture was stirred at the same temperature for 20 minutes. To the resulting solution was added 3-nitrobenzyl chloride (3.77 g, 22 mmol) and the mixture was stirred at room temperature for 20 minutes. This reaction mixture was poured in saturated aqueous ammonium chloride solution (40 mL) and extracted with 3 portions of ethyl acetate. The pooled organic layer was washed with water and saturated aqueous NaCl solution, dried over anhydrous magnesium sulfate (MgSO$_4$), filtered, and concentrated under reduced pressure. The residue was crystallized from ethyl acetate-diisopropyl ether to provide 4.81 g (yield 71%) of the title compound. m.p. 123.5°–125.5° C.

$^1$H NMR (CDCl$_3$) δ: 1.9–2.2 (3H, m), 2.6–2.85 (3H, m), 3.05–3.15 (1H, m), 5.11 (1H, d, J=16.2 Hz), 5.30 (1H, d, J=16.2 Hz), 7.1–7.4 (5H, m), 7.45 (1H, t, J=7.5 Hz), 7.98 (1H, t, J=1.6 Hz), 8.07 (1H, dt, J=7.7, 1.8 Hz).

Reference Example 3

9-[2-[4-(Benzyloxycarbonylamino)phenyl]ethyl]-2,3,9,10a-tetrahydrobenzo[b]cyclopenta[e][1,4]diazepin-10(1H)-one To a solution of 2,3,9,10a-tetrahydrobenzo[cyclopenta[e][1,4]diazepin-10(1H)-one (3.2 g, 16 mmol) in DMF (20 mL) was added sodium hydride (content 60%, 0.67 g, 16.8 mmol) and the mixture was stirred at room temperature for 10 minutes. Then, a solution of 2-[4-(benzyloxycarbonylamino)phenyl]ethyl methanesulfonate (5.5 g, 15.7 mmol) in DMF (5 mL) was added and the mixture was further stirred at 60° C. for 2 hours. This reaction mixture was cooled, diluted with water, and extracted with ethyl acetate. The extract was washed with water and dried and the solvent was distilled off. The residue was crystallized from ethyl acetate-hexane to provide 1.6 g (yield 22%) of the title compound. m.p. 103°–105° C.

$^1$H NMR (CDCl$_3$) δ: 1.70–2.10 (4H, m), 2.50–3.00 (5H, m), 3.85 (1H, ddd, J=14.0, 9.2, 5.2 Hz), 4.46 (1H, dt, J=14.0, 8.2 Hz), 5.48 (2H, s), 6.74 (1H, s), 7.03 (2H, d, J=8.4 Hz), 7.10–7.50 (11H, m).

Reference Example 4

(3aR*,10aS*)-9-(4-Nitrobenzyl)-2,3,3a,4,9,10a-hexahydrobenzo[b]cyclopenta[e][1,4]diazepin-10(1H)-one To a suspension of 9-(4-nitrobenzyl)-2,3,9,10a-tetrahydrobenzo[b]cyclopenta(e][1,4]diazepin-10(1H)-one (10.2 g, 30 mmol) and bromocresol green in a mixture of methanol (100 mL)-tetrahydrofuran (THF) (30 mL) was added sodium cyanoborohydride (2.08 g, 33 mmol). To this mixture, 10% hydrogen chloride/methanol was slowly added dropwise at the same temperature until the color of the reaction mixture had ceased to change. This reaction mixture was diluted with water and extracted with 3 portions of ethyl acetate. The pooled organic layer was washed serially with water and saturated aqueous NaCl solution, dried over MgSO$_4$, filtered, and concentrated under reduced pressure. The residue was purified by silica gel column chromatography (hexane-ethyl acetate=2:1) and crystallized from ethyl acetate-diethyl ether to provide 7.09 g (yield 70%) of the title compound. m.p. 154°–155° C.

$^1$H NMR (CDCl$_3$) δ: 1.5–2.1 (5H, m), 2.3–2.5 (1H, m), 2.9–3.0 (1H, m), 3.50 (1H, br s), 3.9–4.1 (1H, m), 4.91 (1H, d, J=16.0 Hz), 5.17 (1H, d, J=16.6 Hz), 6.9–7.2 (4H, m), 7.45–7.55 (2H, m), 8.0–8.15 (2H, m).

Reference Example 5

(3aR*,10aS*)-9-(3-Nitrobenzyl)-2,3,3a,4,9,10a-hexahydrobenzo[b]cyclopenta[e][1,4]diazepin-10(1H)-one Using 9-(3-nitrobenzyl)-2,3,9,10a-tetrahydrobenzo-[b]cyclopenta[e][1,4]diazepin-10(1H)-one, the title compound was synthesized in otherwise the same manner as Reference Example 4. Yield 86%, m.p. 169°–171° C. (diethyl ether).

$^1$H NMR (CDCl$_3$) δ: 1.46–2.18 (5H, m), 2.32–2.55 (1H, m), 2.93–3.05 (1H, m), 3.69 (1H, br s), 3.93–4.12 (1H, m), 4.88 (1H, d, J=16.2 Hz), 5.49 (1H, d, J=16.2 Hz), 6.91–7.47 (5H, m), 7.65 (1H, d, J=6.8 Hz), 7.99 (1H, d, J=8.0 Hz), 8.34 (1H, s).

Reference Example 6

(3aR*,10aS*)-9-[2-[4-(Benzyloxycarbonylamino)-phenyl]ethyl]-2,3,3a,4,9,10a-hexahydrobenzo[b]cyclopenta[e][1,4]diazepin-10(1H)-one The title compound was synthesized by the same procedure as described in Reference Example 4. Yield=quantitative, oil.

$^1$H NMR (CDCl$_3$) δ: 1.40–2.10 (6H, m), 2.30–2.50 (1H, m), 2.60–3.00 (3H, m), 3.72 (1H, ddd, J=13.4, 10.2, 5.2 Hz), 3.80–4.00 (1H, m), 4.22 (1H, d, dd, J=13.4, 10.2, 6.4 Hz), 5.18 (2H, s), 6.69 (1H, s), 6.85–7.00 (11H, m), 7.00–7.50 (12H, m).

Reference Example 7

(3aR*,10aS*)-9-(4-Aminobenzyl)-2,3,3a,4,9,10a-hexahydrobenzo[b]cyclopenta[e][1,4]diazepin-10(1H)-one (3aR*,10aS*)-9-(4-Nitrobenzyl)-2,3,3a,4,9,10a-hexahydrobenzo[b]cyclopenta[e][1,4]diazepin-10(1H)-one (5.06 g, 15 mmol) and 10% palladium-on-carbon (hydrous) (0.5 g) were suspended in THF (15 mL)-methanol (15 mL) and the suspension was stirred under hydrogen at room temperature for 4.5 hours. The catalyst was then filtered off and the filtrate was concentrated under reduced pressure. The residue was crystallized from ethyl acetate-hexane to provide 3.27 g (yield 71%) of the title compound. m.p. 149.1°–149.6° C.

$^1$H NMR (CDCl$_3$) δ: 1.4–2.1 (5H, m), 2.35–2.6 (1H, m), 2.85–3.0 (1H, m), 3.96 (1H, ddd, J=10.1, 7.9, 6.6 Hz), 4.95 (2H, s), 6.56 (2H, d, J=8.4 Hz), 6.8–7.2 (6H, m).

The amino proton resonance was too broad to be identified.

Reference Example 8

(3aR*,10aS*)-9-(3-Aminobenzyl)-2,3,3a,4,9,10a-hexahydrobenzo[b]cyclopenta[e][1,4]diazepin-10(1H)-one Using (3aR*,10aS*)-9-(3-nitrobenzyl)-2,3,3a,4,9,10a-hexahydrobenzo[b]cyclopenta[e][1,4]diazepin-10(1H)-one, the title compound was synthesized in otherwise the same manner as Reference Example 7. Yield 84%, m.p. 176°–178° C. (diethyl ether).

$^1$H NMR (CDCl$_3$) δ: 1.50–2.13 (5H, m), 2.35–2.57 (1H, m), 2.89–3.01 (1H, m), 3.43 (3H, br s), 3.90–4.07 (1H, m), 4.83 (1H, d, J=15.8 Hz), 5.10 (1H, d, J=15.8 Hz), 6.51 (1H, d, J=6.6 Hz), 6.63–6.69 (2H, m), 6.87–7.17 (5H, m)

Reference Example 9

(3aR*,10aS*)-9-[4-(Benzyloxycarbonylamino)benzyl]-2,3,3a,4,9,10a-hexahydrobenzo[b]cyclopenta[e][1,4]diazepin-10(1H)-one To a solution of (3aR*,10aS*)-9-(4-aminobenzyl)-2,3,3a, 4,9,10a-hexahydrobenzo[b]cyclopenta[e][1,4]diazepin-10 (1H)-one (3.64 g, 12 mmol) in dichloromethane (15 mL) was added a solution of sodium carbonate (1.88 g, 18 mmol) in water (15 mL) at 0° C. To this mixture was added benzyl chloroformate (2.0 mL, 14 mmol) at the same temperature and the mixture was stirred at 0° C. for 15 minutes. Upon phase separation, the aqueous layer was extracted with dichloromethane and the pooled organic layer was dried over MgSO₄, filtered, and concentrated under reduced pressure. The residue was crystallized from ethyl acetate-hexane to provide 4.18 g (yield 79%) of the title compound. m.p. 161.7°–162.5° C.

$^1$H NMR (CDCl₃) δ: 1.4–2.1 (5H, m), 2.35–2.55 (1H, m), 2.85–3.0 (1H, m), 3.9–4.05 (1H, m), 4.93 (1H, d, J=15.6 Hz), 5.10 (1H, d, J=15.6 Hz), 5.17 (2H, s), 6.67 (1H, br s), 6.8–7.45 (13H, m).

The signal of amino protons was too broad for resolution.

Reference Example 10

(3aR*,10aS*)-9-[3-(Benzyloxycarbonylamino)benzyl]-2,3, 3a,4,9,10a-hexahydrobenzo[b]cyclopenta[e][1,4]diazepin-10(1H)-one Using (3aR*,10aS*)-9-(3-aminobenzyl)-2,3,3a,4,9,10a-hexahydrobenzo[b]cyclopenta[e][1,4]diazepin-10(1H)-one, the title compound was synthesized in otherwise the same manner as Reference Example 9. Yield 82%, m.p. 179°–180° C. (diethyl ether).

$^1$H NMR (CDCl₃) δ: 1.45–2.10 (5H, m), 2.38–2.54 (1H, m), 2.89–3.02 (1H, m), 3.32–3.5 (1H, br), 3.91–4.06 (1H, m), 5.04 (2H, s), 5.17 (2H, s), 6.69 (1H, br s), 6.87–7.45 (13H, m).

Reference Example 11

(3aR*,10aS*)-9-[4-(Phenoxycarbonylamino)benzyl]-2,3, 3a,4,9,10a-hexahydrobenzo[b]cyclopenta[e][1,4]diazepin-10(1H)-one Using phenyl chloroformate, the title compound was synthesized in otherwise the same manner as Reference Example 9. Yield 87%, m.p. 183°–184° C. (ethyl acetate-diethyl ether).

$^1$H NMR (DMSO-d₆) δ: 1.4–2.05 (5H, m), 2.1–2.3 (1H, m), 2.75–2.9 (1H, m), 3.75–3.95 (1H, m), 4.82 (1H, d, J=15.8 Hz), 5.1–5.3 (1H, br), 5.18 (1H, d, J=15.8 Hz), 6.9–7.1 (3H, m), 7.15–7.5 (10H, m), 10.11 (1H, br s).

Reference Example 12

(3aR*,10aS*)-9-[4-(Benzyloxycarbonylamino)benzyl]-4-(bromoacetyl)-2,3,3a,4,9,10a-hexahydrobenzo[b] cyclopenta[e][1,4]diazepin-10(1H)-one To a solution of (3aR*,10aS*)-9-[4-(benzyloxycarbonylamino)benzyl]-2,3,3a,4,9,10a-hexahydrobenzo[b]cyclopenta[e][1,4]diazepin-10(1H)-one (610 mg, 1.4 mmol) in dichloromethane (7 mL) was added bromoacetyl bromide (0.15 mL, 1.7 mmol) dropwise and the mixture was stirred at room temperature for 15 minutes. This reaction mixture was diluted with water (5 mL) with vigorous stirring and neutralized with sodium hydrogen carbonate. The aqueous layer was separated and the organic layer was washed with water, dried over MgSO₄, filtered, and concentrated under reduced pressure. The residue was recrystallized from chloroform-ethyl acetate to provide 519 mg (yield 66%) of the title compound. m.p. 222°–223° C. (decomp.).

$^1$H NMR (CDCl₃) δ: 1.0–1.9 (5H, m), 2.0–2.25 (1H, m), 2.84 (1H, d, J=11.8 Hz), 3.03 (1H, d, J=11.8 Hz), 3.15 (1H, dt, J=12.1, 9.1 Hz), 4.64 (1H, d, J=15.0 Hz), 5.18 (2H, s), 5.48 (1H, d, J=15.0 Hz), 5.81 (1H, ddd, J=9.3, 8.3, 3.9 Hz), 6.68 (1H, br s), 7.1–7.5 (13H, m).

Reference Example 13

(3aR*,10aS*)-4-(Chloroacetyl)-9-[4-(phenoxycarbonylamino)benzyl]-2,3,3a,4,9,10a-hexahydrobenzo[b]cyclopenta[e][1,4]diazepin-10(1H)-one To a solution of (3aR*,10aS*)-9-[4-(phenoxycarbonylamino)benzyl]-2,3,3a,4,9,10a-hexahydrobenzo[b]cyclopenta[e][1,4]diazepin-10(1H)-one (1.61 g, 3.8 mmol) in DMF (20 mL) was added chloroacetyl chloride (0.36 mL, 4.5 mmol) and the mixture was stirred at room temperature for 2 hours. This reaction mixture was diluted with saturated aqueous NaHCO₃ solution and extracted with 3 portions of chloroform. The pooled organic layer was washed with 2 portions of water and, then, with saturated aqueous NaCl solution. This solution was dried over MgSO₄, filtered, and concentrated under reduced pressure. The residue was crystallized from chloroform-diethyl ether to provide 0.90 g (yield 47%) of the compound. m.p. 207–210° C.

$^1$H NMR (CDCl₃) δ: 1.0–1.5 (3H, m), 1.5–1.9 (2H, m), 2.0–2.25 (1H, m), 2.75 (1H, d, J=13.6 Hz), 3.16 (1H, dt, J=12.1, 9.1 Hz), 3.36 (1H, d, J=13.6 Hz), 4.55 (1H, d, J=14.9 Hz), 5.61 (1H, d, J=14.9 Hz), 5.83 (1H, td, J=8.7, 4.1 Hz), 6.8–7.5 (14H, m).

Reference Example 14

(3aR*,10aS*)-9-(4-Aminobenzyl)-4-(phthalimidoacetyl)-2, 3,3a,4,9,10a-hexahydrobenzo[b]cyclopenta[e]-[1,4] diazepin-10(1H)-one hydrobromide To a solution of (3aR*,10aS*)-9-[4-(benzyloxycarbonylamino)benzyl]-4-(phthalimidoacetyl)-2, 3,3a,4,9,10a-hexahydrobenzo[b]cyclopenta[e][1,4] diazepin-10(1H)-one (366 mg, 0.58 mmol) in chloroform (3 mL) was added 25% hydrogen bromide/acetic acid (1 mL) and the mixture was stirred at room temperature for 75 minutes. This reaction mixture was concentrated under reduced pressure and the residue was crystallized from ethanoldiethyl ether to provide 309 mg (yield 92%) of the title compound. m.p. 222°–224° C.

$^1$H NMR (DMSO-d₆) δ: 1.0–1.5 (3H, m), 1.5–1.9 (2H, m), 1.9–2.15 (1H, m), 3.0–3.25 (1H, m), 3.34 (1H, d, J=16.7 Hz), 4.19 (1H, d, J=16.7 Hz), 5.16 (2H, s), 5.63 (1H, ddd, J=9.2, 8.4, 3.8 Hz), 7.0–7.6 (8H, m), 7.85–8.0 (4H, m).

The amino proton resonance was too broad to be identified.

Reference Example 15

(3aR*,10aS*)-9-(3-Aminobenzyl)-4-(phthalimidoacetyl)-2, 3,3a,4,9,10a-hexahydrobenzo[b]cyclopenta[e]-[1,4] diazepin-10(1H)-one hydrobromide Using (3aR*,10aS*)-9-[3-(benzyloxycarbonylamino)-benzyl]-4-(phthalimidoacetyl)-2,3,3a, 4,9,10a-hexahydrobenzo[b]cyclopenta[e][1,4]diazepin-10(1H)-one, the title compound was synthesized in otherwise the same manner as Reference Example 14. Yield 85%, m.p. 280°–282° C. (decomp.) (diethyl ether).

$^1$H NMR (DMSO-d₆) δ: 1.02–1.45 (3H, m), 1.59–1.95 (2H, m), 1.98–2.17 (1H, m), 3.05–3.21 (1H, m), 3.41 (1H, d, J=16.8 Hz), 3.42–3.6 (2H, br), 4.19 (1H, d, J=16.8 Hz), 4.95 (1H, d, J=16.2 Hz), 5.34 (1H, d, J=16.2 Hz), 5.59–5.77 (1H, m), 7.19–7.37 (3H, m), 7.39–7.70 (5H, m), 7.81–8.02 (4H, m), 9.60 (1H, br s).

Reference Example 16

(3aR*,10aS*)-9-(4-Aminobenzyl)-4-(phthalimidoacetyl)-2, 3,3a,4,9,10a-hexahydrobenzo[b]cyclopenta[e]-[1,4] diazepin-10(1H)-one To a solution of (3aR*,10aS*)-9-[4-(benzyloxycarbonylamino)benzyl]-4-(phthalimidoacetyl)-2, 3,3a,4,9,10a-hexahydrobenzo[b]cyclopenta[e][1,4]
diazepin-10(1H)-one (5.15 g, 8.2 mmol) in chloroform (80
mL) was added 25% hydrogen bromide/acetic acid (15 mL)
and the mixture was stirred at room temperature for 45
minutes. This reaction mixture was concentrated under
reduced pressure and the residue was crystallized from
ethanol-diethyl ether to provide (3aR*,10aS*)-9-(4-
aminobenzyl)-4-(phthalimidoacetyl)-2,3,3a,4,9,10a-
hexahydrobenzo[b]cyclopenta[e][1,4]diazepin-10(1H)-one
hydrobromide. This product was suspended in chloroform
and treated with 0.5N-aqueous NaOH solution (40 mL). The
aqueous layer was separated and the organic layer was
washed with water, dried over MgSO$_4$, filtered, and concentrated under reduced pressure. The residue was crystallized from chloroform-diethyl ether to provide 3.71 g (yield
91%) of the title compound. m.p. 286°–289° C.

$^1$H-NMR (CDCl$_3$) δ: 1.0–1.45 (3H, m), 1.5–1.9 (2H, m),
2.0–2.2 (1H, m), 3.13 (1H, dt, J=11.9, 9.1 Hz), 3.30 (1H, d,
J=16.5 Hz), 3.65 (2H, br s), 3.90 (1H, d, J=16.5 Hz), 4.58
(1H, d, J=14.8 Hz), 5.56 (1H, d, J=14.8 Hz), 5.74 (1H, td,
J=8.6, 3.7 Hz), 6.64 (2H, d, J=8.0 Hz), 7.07 (2H, d, J=8.4
Hz), 7.2–7.35 (1H, m), 7.35–7.5 (3H, m), 7.65–7.9 (4H, m).

Reference Example 17

(3aR*,10aS*)-9-(4-Aminobenzyl)-4-(2H-1,3-dioxo-1,3,4,5,
6,7-hexahydroisoindole-2-acetyl)-2,3,3a,4,9,10a-
hexahydrobenzo[b]cyclopenta[e][1,4]diazepin-10(1H)-one Using (3aR*,10aS*)-9-[4-(benzyloxycarbonylamino)-
benzyl]-4-(2H-1,3-dioxo-1,3,4,5,6,7-hexahydroisoindole-2-
acetyl)-2,3,3a,4,9,10a-hexahydrobenzo[b]cyclopenta[e][1,
4]diazepin-10(1H)-one, the title compound was synthesized
in otherwise the same manner as Reference Example 16.
Yield 96%, m.p. 262°–265° C. (chloroform-diethyl ether).

$^1$H NMR (CDCl$_3$) δ: 1.0–1.45 (3H, m), 1.5–1.9 (6H, m),
2.0–2.2 (1H, m), 2.25–2.4 (4H, m), 2.6–3.2 (2H, br), 3.0–3.2
(1H, m), 3.08 (1H, d, J=16.4 Hz), 3.70 (1H, d, J=16.4 Hz),
4.56 (1H, d, J=14.6 Hz), 5.54 (1H, d, J=14.6 Hz), 5.72 (1H,
td, J=8.7, 4.0 Hz), 6.62 (2H, d, J=8.4 Hz), 7.04 (2H, d, J=8.4
Hz), 7.2–7.5 (4H, m).

Reference Example 18

(3aR*,10aS*)-9-[4-(3-Benzyl-3-methylureido)benzyl]-2,3,
3a,4,9,10a-hexahydrobenzo[b]cyclopenta[e][1,4]diazepin-
10(1H)-one To a solution of (3aR*,10aS*)-9-[4-
(phenoxycarbonylamino)benzyl]-2,3,3a,4,9,10a-
hexahydrobenzo[b]cyclopenta[e][1,4]diazepin-10(1H)-one
(0.43 g, 1 mmol) in DMF (5 mL) was added
N-benzylmethylamine (0.14 mL, 1.1 mmol) and the mixture
was stirred at room temperature for 84 hours. This reaction
mixture was diluted with ethyl acetate and washed with 2
portions of water and, then, with saturated aqueous NaCl
solution. This solution was dried over MgSO$_4$, filtered, and
concentrated under reduced pressure. The residue was purified by silica gel column chromatography (hexane-ethyl
acetate=1:1) to provide 0.30 g (yield 66%) of the title
compound. Amorphous.

$^1$H NMR (CDCl$_3$) δ: 1.4–2.1 (5H, m), 2.35–2.5 (1H, m),
2.85–3.05 (1H, m), 3.00 (3H, s), 3.3–3.5 (1H, br), 3.9–4.05
(1H, m), 4.57 (2H, s), 4.95 (1H, d, J=15.3 Hz), 5.07 (1H, d,
J=15.3 Hz), 6.28 (1H, br s), 6.8–7.4 (13H, m).

Reference Example 19

(3aR*,10aS*)-4-(Chloroacetyl)-9-[4-[3-(2-phenylethyl)
ureido]benzyl]-2,3,3a,4,9,10a-hexahydrobenzo[b]-
cyclopenta[e][1,4]diazepin-10(1H)-one To a solution of (3aR*,10aS*)-4-(chloroacetyl)-9-[4-
(phenoxycarbonylamino)benzyl]-2,3,3a,4,9,10a-
hexahydrobenzo[b]cyclopenta[e][1,4]diazepin-10(1H)-one
(151 mg, 0.3 mmol) in DMF (1.5 mL) was added
2-phenylethylamine (38 µl, 0.3 mmol) and the mixture was
stirred at room temperature for 4 hours. This reaction
mixture was diluted with ethyl acetate and washed with 2
portions of water and, then, with saturated aqueous NaCl
solution. This solution was dried over NaSO$_4$ and concentrated under reduced pressure and the residue was crystallized from ethanol-diethyl ether to provide 62 mg (yield
39%) of the title compound. m.p. 224°–226° C.

$^1$H NMR (CDCl$_3$) δ: 1.0–1.45 (3H, m), 1.45–1.9 (2H, m),
1.95–2.2 (1H, m), 2.60 (1H, d, J=13.8 Hz), 2.80 (2H, t, J=7.0
Hz), 3.0–3.1 (1H, m), 3.33 (1H, d, J=13.8 Hz), 3.45 (2H, q,
J=6.5 Hz), 4.45 (1H, d, J=14.6 Hz), 5.25–5.4 (1H, m), 5.59
(1H, d, J=14.6 Hz), 5.74 (1H, td, J=8.6, 3.6 Hz), 7.0–7.6
(14H, m).

Reference Example 20

(3aR*,10aS*)-4-(Chloroacetyl)-9-[4-[3-(4-fluorobenzyl)
ureido]benzyl]-2,3,3a,4,9,10a-hexahydrobenzo[b]-
cyclopenta[e][1,4]diazepin-10(1H)-one Using 4-fluorobenzylamine, the title compound was synthesized in otherwise the same manner as Reference
Example 19. Yield 37%, m.p. 202°–203° C. (ethyl acetate-
diethyl ether).

$^1$H NMR (DMSO-d$_6$) δ: 0.9–2.1 (6H, m), 2.71 (1H, d,
J=14.1 Hz), 3.0–3.1 (1H, m), 3.75 (1H, d, J=14.1 Hz), 4.24
(2H, d, J=5.8 Hz), 4.62 (1H, d, J=15.0 Hz), 5.38 (1H, d,
J=15.0 Hz), 5.55–5.75 (1H, m), 6.57 (1H, t, J=5.8 Hz), 6.97
(2H, d, J=8.4 Hz), 7.1–7.45 (6H, m), 7.13 (2H, t, J=8.8 Hz),
7.52 (1H, t, J=7.7 Hz), 7.64 (1H, d, J=7.6 Hz), 8.52 (1H, s).

Reference Example 21

(3aR*,10aS*)-4-(Chloroacetyl)-9-[4-[3-(4-methoxybenzyl)
ureido]benzyl]-2,3,3a,4,9,10a-hexahydrobenzo[b]-
cyclopenta[e][1,4]diazepin-10(1H)-one Using 4-methoxybenzylamine, the title compound was
synthesized in otherwise the same manner as Reference
Example 19. Yield 43%, m.p. 225°–226° C. (ethyl acetate)

$^1$H-NMR (CDCl$_3$) δ: 0.9–1.6 (4H, m), 1.6–2.05 (2H, m),
2.56 (1H, d, J=13.9 Hz), 2.98 (1H, dt, J=11.7, 9.0 Hz), 3.30
(1H, d, J=13.9 Hz), 3.76 (3H, s), 4.33 (2H, d, J=5.6 Hz), 4.43
(1H, d, J=14.4 Hz), 5.5–5.7 (1H, m), 5.60 (1H, d, J=14.4
Hz), 5.73 (1H, t, J=5.3 Hz), 6.83 (2H, d, J=8.8 Hz), 6.95–7.1
(3H, m), 7.15–7.35 (6H, m), 7.4–7.55 (2H, m).

Reference Example 22

4-(Benzyloxycarbonylamino)phenethyl methanesulfonate

In dichloromethane (50 mL) was suspended
4-aminophenethyl alcohol (5 g, 36.4 mmol) followed by
addition of carbobenzoxy chloride (6.5 g, 38.2 mmol) at 0°
C. This reaction mixture was stirred for 30 minutes, at the
end of which time it was diluted with water. The organic
layer was taken, washed with water, dried, and concentrated.
The residue was dissolved in dichloromethane (30 mL), and
triethylamine (4.5 mL) and mesyl chloride (1.36 mL) were
added under ice-cooling, followed by stirring for 30 minutes. This reaction mixture was washed serially with
1N-HCl and saturated aqueous NaHCO$_3$ solution, dried, and
concentrated. Yield 6.0 g (47%). The title compound thus
obtained was not purified but directly submitted to the next
reaction.

$^1$H NMR (CDCl$_3$) δ: 2.86 (3H, s), 3.01 (2H, t, J=6.8 Hz),
4.38 (2H, t, J=6.8 Hz), 5.20 (2H, s), 6.71 (1H, broad s), 7.15
(2H, d, J=8.4 Hz), 7.30–7.50 (7H, m).

Example 1

(3aR*,10aS*)-9-[4-(Benzyloxycarbonylamino)benzyl]-4-
(phthalimidoacetyl)-2,3,3a,4,9,10a-hexahydrobenzo[b]
cyclopenta[e][1,4]diazepin-10(1H)-one (3aR*,10aS*)-9-[4-(Benzyloxycarbonylamino)benzyl]-4-(bromoacetyl)-2,3,3a,4,9,10a-hexahydrobenzo[b]cyclopenta[e][1,4]diazepin-10(1H)-one (496 mg, 0.88 mmol) and potassium phthalimide (172 mg, 0.93 mmol) were suspended in DMF (3 mL) and the suspension was stirred at room temperature for 1 hour. This reaction mixture was diluted with water and extracted with 3 portions of chloroform. The pooled organic layer was washed with water, dried over $MgSO_4$, filtered, and concentrated under reduced pressure. The residue was crystallized from ethanol to provide 495 mg (yield 89%) of the title compound. m.p. 144°–147° C.

$^1$H NMR (CDCl$_3$) δ: 1.0–1.5 (3H, m), 1.5–1.9 (2H, m), 1.95–2.2 (1H, m), 3.05–3.25 (1H, m), 3.14 (1H, d, J=16.5 Hz), 3.91 (1H, d, J=16.5 Hz), 4.74 (1H, d, J=15.0 Hz), 5.10 (2H, s), 5.53 (1H, d, J=15.0 Hz), 5.75 (1H, td, J=8.6, 3.6 Hz), 6.90 (1H, br s), 7.15–7.5 (13H, m), 7.6–7.9 (4H, m).

Example 2

(3aR*,10aS*)-9-[4-(Benzyloxycarbonylamino)benzyl]-4-(2H-1,3-dioxo-1,3,4,5,6,7-hexahydroisoindole-2-acetyl)-2,3,3a,4,9,10a-hexahydrobenzo[b]cyclopenta[e][1,4]diazepin-10(1H)-one To a solution of 3,4,5,6-tetrahydrophthalimide (0.50 g, 3.3 mmol) in DMF (10 mL) was added sodium hydride (60% dispersion in liquid paraffin, 0.12 g, 3 mmol) at 0° C. and the mixture was stirred at the same temperature for 15 minutes. To this solution was added (3aR*,10aS*)-9-[4-(benzyloxycarbonylamino)benzyl]-4-(bromoacetyl)-2,3,3a,4,9,10a-hexahydrobenzo[b]cyclopenta[e][1,4]diazepin-10(1H)-one (1.69, 3 mmol) and the mixture was further stirred at room temperature for 30 minutes. This reaction mixture was poured in saturated aqueous ammonium chloride solution (15 mL), diluted with water, and extracted with 3 portions of ethyl acetate. The pooled organic layer was washed with water and saturated aqueous NaCl solution, dried over $MgSO_4$, filtered, and concentrated under reduced pressure. The residue was crystallized from ethyl acetate-diethyl ether to provide 1.64 g (yield 86%) of the title compound. m.p. 170°–172° C.

$^1$H NMR (CDCl$_3$) δ: 1.0–1.5 (3H, m), 1.5–1.9 (6H, m), 1.95–2.2 (1H, m), 2.2–2.4 (4H, m), 2.94 (1H, d, J=16.9 Hz), 3.13 (1H, dt, J=12.0, 9.0 Hz), 3.71 (1H, d, J=16.9 Hz), 4.72 (1H, d, J=15.0 Hz), 5.14 (2H, s), 5.50 (1H, d, J=15.0 Hz), 5.65–5.8 (1H, m), 6.88 (1H, br s), 7.1–7.5 (13H, m)

Example 3

(3aR*,10aS*)-9-[3-(Benzyloxycarbonylamino)benzyl]-4-(phthalimidoacetyl)-2,3,3a,4,9,10a-hexahydrobenzo[b]cyclopenta[e][1,4]diazepin-10(1H)-one To a solution of (3aR*,10aS*)-9-[3-(benzyloxycarbonylamino)benzyl]-2,3,3a,4,9,10a-hexahydrobenzo[b]cyclopenta[e][1,4]diazepin-10(1H)-one (1.9 g, 4.3 mmol) in 1,2-dichloroethane (50 mL) was added phthalimidoacetyl chloride (1.1 g, 4.7 mmol) at room temperature and the mixture was refluxed for 17 hours. After cooling, saturated aqueous NaHCO$_3$ solution (30 mL) was added and the mixture was diluted with water and extracted with 2 portions of chloroform. The pooled organic layer was washed with saturated aqueous NaCl solution, dried over $MgSO_4$, filtered, and concentrated under reduced pressure. The residue was crystallized from diethyl ether to provide 1.5 g (yield 55%) of the title compound. m.p. 224°–225° C.

$^1$H NMR (CDCl$_3$) δ: 1.05–1.47 (3H, m), 1.59–1.93 (2H, m), 2.01–2.21 (1H, m), 3.12 (1H, dt, J=11.8, 8.8 Hz), 3.46 (1H, d, J=16.4 Hz), 4.18 (1H, d, J=16.4 Hz), 4.49 (1H, d, J=15.2 Hz), 5.09 (1H, s), 5.46 (1H, d, J=15.2 Hz), 5.71–5.84 (1H, m), 6.99 (1H, d, J=7.6 Hz), 7.14–7.52 (14H, m), 7.59–7.85 (4H, m)

Example 4

(3aR*,10aS*)-9-[2-[4-(Benzyloxycarbonylamino)-phenyl]ethyl]-4-(phthalimidoacetyl)-2,3,3a,4,9,10a-hexahydrobenzo[b]cyclopenta[e][1,4]diazepin-10(1H)-one Using (3aR*,10aS*)-9-[2-[4-(benzyloxycarbonylamino)phenyl]ethyl]-2,3,3a,4,9,10a-hexahydrobenzo[b]cyclopenta[e][1,4]diazepin-10(1H)-one, the title compound was synthesized in otherwise the same manner as Example 3. Yield 33%, m.p. 152°–154° C. (chloroform-ethyl acetate).

$^1$H NMR (CDCl$_3$) δ: 0.90–1.40 (4H, m), 1.50–1.80 (2H, m), 2.60–2.70 (1H, m), 2.70–3.30 (2H, m), 3.71 (1H, d, J=16.8 Hz), 3.80–4.30 (2H, m), 4.34 (1H, d, J=16.8 Hz), 5.14 (2H, s), 5.65 (1H, m), 7.18 (2H, d, J=8.4 Hz), 7.30–7.70 (11H, m), 7.87 (4H, m), 9.72 (1H, s).

Example 5

(3aR*,10aS*)-9-(4-Acetamidobenzyl)-4-(phthalimidoacetyl)-2,3,3a,4,9,10a-hexahydrobenzo[b]cyclopenta[e]-[1,4]diazepin-10(1H)-one To a suspension of (3aR*,10aS*)-9-(4-aminobenzyl)-4-(phthalimidoacetyl)-2,3,3a,4,9,10a-hexahydrobenzo[b]cyclopenta[e][1,4]diazepin-10(1H)-one (198 mg, 0.4 mmol) in dichloromethane (1 mL) was added acetyl chloride (43 μL, 0.6 mmol) and the mixture was stirred at room temperature for 20 minutes. This reaction mixture was diluted with dichloromethane (3 mL) and, after saturated aqueous NaHCO$_3$ solution (2 mL) was added, the mixture was further stirred. The aqueous layer was then separated and the organic layer was washed with water, dried over $MgSO_4$, and concentrated under reduced pressure. The residue was crystallized from dichloromethane-ethanol and recrystallized from chloroform-ethanol to provide 72 mg (yield 34%) of the title compound. m.p. 303°–306° C.

$^1$H NMR (CDCl$_3$) δ: 1.0–1.45 (3H, m), 1.55–1.9 (2H, m), 2.0–2.2 (1H, m), 2.09 (3H, s), 3.05 (1H, d, J=16.5 Hz), 3.14 (1H, dt, J=12.0, 9.0 Hz), 3.83 (1H, d, J=16.5 Hz), 4.66 (1H, d, J=14.8 Hz), 5.62 (1H, d, J=14.8 Hz), 5.75 (1H, ddd, J=8.9, 8.3, 3.9 Hz), 7.2–7.4 (3H, m), 7.4–7.55 (5H, m), 7.63 (1H, br s), 7.65–7.9 (4H, m).

Example 6

(3aR*,10aS*)-4-(Phthalimidoacetyl)-9-(4-propionamidobenzyl)-2,3,3a,4,9,10a-hexahydrobenzo[b]cyclopenta[e][1,4]diazepin-10(1H)-one To a suspension of (3aR*,10aS*)-9-(4-aminobenzyl)-4-(phthalimidoacetyl)-2,3,3a,4,9,10a-hexahydrobenzo[b]cyclopenta[e][1,4]diazepin-10(1H)-one (148 mg, 0.3 mmol) and triethylamine (50 μL, 0.36 mmol) in dichloromethane (3 mL) was added propionyl chloride (28 μL, 0.33 mmol) and the mixture was stirred at room temperature for 10 minutes. This reaction mixture was diluted with water and stirred. The aqueous layer was separated and the organic layer was dried over NaSO$_4$ and concentrated under reduced pressure. The residue was crystallized from dichloromethane-ethanol-diethyl ether to provide 131 mg (yield 79%) of the title compound. m.p. 286.0°–286.5° C.

$^1$H NMR (CDCl$_3$) δ: 1.0–1.5 (3H, m), 1.16 (3H, t, J=7.5 Hz), 1.55–1.9 (2H, m), 2.0–2.2 (1H, m), 2.32 (2H, q, J=7.5 Hz), 3.02 (1H, d, J=16.5 Hz), 3.05–3.25 (1H, m), 3.81 (1H, d, J=16.5 Hz), 4.63 (1H, d, J=14.8 Hz), 5.65 (1H, d, J=14.8 Hz), 5.65–5.85 (1H, m), 7.15–7.6 (9H, m), 7.65–7.9 (4H, m).

Example 7

(3aR*,10aS*)-9-(4-Benzamidobenzyl)-4-(phthalimidoacetyl)-2,3,3a,4,9,10a-hexahydrobenzo[b]cyclopenta[e]-[1,4]diazepin-10(1H)-one Using benzoyl chloride, the title compound was synthesized in otherwise the same manner as Example 5. Yield 54%, m.p. 252°–255° C. (dichloromethane-ethanol).

¹H NMR (CDCl₃) δ: 1.0–1.5 (3H, m), 1.5–1.9 (2H, m), 2.0–2.2 (1H, m), 2.96 (1H, d, J=16.4 Hz), 3.14 (1H, dt, J=11.9, 9.1 Hz), 3.80 (1H, d, J=16.4 Hz), 4.58 (1H, d, J=14.6 Hz), 5.65–5.85 (1H, m), 5.77 (1H, d, J=14.6 Hz), 7.2–7.55 (9H, m), 7.60 (2H, d, J=8.4 Hz), 7.65–7.8 (4H, m), 7.8–7.9 (2H, m), 8.27 (1H, br s).

Example 8

(3aR*,10aS*)-9-[4-(2-Fluorobenzamido)benzyl]-4-(phthalimidoacetyl)-2,3,3a,4,9,10a-hexahydrobenzo[b]cyclopenta[e][1,4]diazepin-10(1H)-one Using 2-fluorobenzoyl chloride, the title compound was synthesized in otherwise the same manner as Example 6. Yield 89%, m.p. 237.6°–239.6° C. (ethanol-diethyl ether).

¹H NMR (CDCl₃) δ: 1.0–1.5 (3H, m), 1.55–1.9 (2H, m), 2.0–2.25 (1H, m), 3.05–3.25 (1H, m), 3.10 (1H, d, J=16.5 Hz), 3.93 (1H, d, J=16.5 Hz), 4.80 (1H, d, J=14.7 Hz), 5.56 (1H, d, J=14.7 Hz), 5.7–5.85 (1H, m), 7.05–7.9 (15H, m), 8.01 (1H, td, J=7.9, 1.7 Hz), 8.45–8.65 (1H, m).

Example 9

(3aR*,10aS*)-9-[4-(3-Fluorobenzamido)benzyl]-4-(phthalimidoacetyl)-2,3,3a,4,9,10a-hexahydrobenzo[b]cyclopenta[e][1,4]diazepin-10(1H)-one Using 3-fluorobenzoyl chloride, the title compound was synthesized in otherwise the same manner as Example 6. Yield 92%, m.p. 256°–259° C. (ethanol-diethyl ether).

¹H NMR (CDCl₃) δ: 1.0–1.5 (3H, m), 1.55–1.9 (2H, m), 2.0–2.25 (1H, m), 2.88 (1H, d, J=16.6 Hz), 3.13 (1H, dt, J=12.2, 9.0 Hz), 3.74 (1H, d, J=16.6 Hz), 4.50 (1H, d, J=14.6 Hz), 5.65–5.85 (1H, m), 5.84 (1H, d, J=14.6 Hz), 7.15–7.85 (16H, m), 8.38 (1H, br s).

Example 10

(3aR*,10aS*)-9-[4-(4-Fluorobenzamido)benzyl]-4-(phthalimidoacetyl)-2,3,3a,4,9,10a-hexahydrobenzo[b]cyclopenta[e][1,4]diazepin-10(1H)-one Using 4-fluorobenzoyl chloride, the title compound was synthesized in otherwise the same manner as Example 6. Yield 84%, m.p. 244.5°–246° C. (ethanol-diethyl ether).

¹H NMR (CDCl₃) δ: 1.0–1.5 (3H, m), 1.5–1.9 (2H, m), 2.0–2.25 (1H, m), 2.92 (1H, d, J=16.6 Hz), 3.0–3.25 (1H, m), 3.77 (1H, d, J=16.6 Hz), 4.55 (1H, d, J=14.7 Hz), 5.65–5.85 (1H, m), 5.79 (1H, d, J=14.7 Hz), 7.05–8.0 (16H, m), 8.30 (1H, br s).

Example 11

(3aR*,10aS*)-9-[4-(4-Chlorobenzamido)benzyl]-4-(phthalimidoacetyl)-2,3,3a,4,9,10a-hexahydrobenzo[b]cyclopenta[e][1,4]diazepin-10(1H)-one Using 4-chlorobenzoyl chloride, the title compound was synthesized in otherwise the same manner as Example 6. Yield 76%, m.p. 191°–194° C. (ethanol-diethyl ether).

¹H NMR (CDCl₃) δ: 1.0–1.5 (3H, m), 1.55–1.9 (2H, m), 2.0–2.25 (1H, m), 2.91 (1H, d, J=16.4 Hz), 3.13 (1H, dt, J=11.9, 9.0 Hz), 3.76 (1H, d, J=16.4 Hz), 4.54 (1H, d, J=14.8 Hz), 5.65–5.8 (1H, m), 5.80 (1H, d, J=14.8 Hz), 7.2–7.6 (10H, m), 7.65–7.9 (6H, m), 8.32 (1H, br s).

Example 12

(3aR*,10aS*)-9-[4-(4-Bromobenzamido)benzyl]-4-(phthalimidoacetyl)-2,3,3a,4,9,10a-hexahydrobenzo[b]cyclopenta[e][1,4]diazepin-10(1H)-one Using 4-bromobenzoyl chloride, the title compound was synthesized in otherwise the same manner as Example 6. Yield 74%, m.p. 175°–180° C. (ethanol).

¹H NMR (CDCl₃) δ: 1.0–1.5 (3H, m), 1.55–1.9 (2H, m), 2.0–2.2 (1H, m), 2.95 (1H, d, J=16.7 Hz), 3.12 (1H, dt, J=11.9, 9.0 Hz), 3.78 (1H, d, J=16.7 Hz), 4.60 (1H, d, J=14.6 Hz), 5.65–5.85 (1H, m), 5.73 (1H, d, J=14.6 Hz), 7.2–7.4 (3H, m), 7.4–7.9 (13H, m), 8.46 (1H, br s).

Example 13

(3aR*,10aS*)-9-[4-(2-Methoxybenzamido)benzyl]-4-(phthalimidoacetyl)-2,3,3a,4,9,10a-hexahydrobenzo[b]cyclopenta[e][1,4]diazepin-10(1H)-one Using 2-methoxybenzoyl chloride, the title compound was synthesized in otherwise the same manner as Example 6. Yield 89%, m.p. 279°–281° C. (ethanol).

¹H NMR (CDCl₃) δ: 1.0–1.5 (3H, m), 1.55–1.9 (2H, m), 2.0–2.25 (1H, m), 3.16 (1H, dt, J=11.7, 9.0 Hz), 3.25 (1H, d, J=16.7 Hz), 3.96 (1H, d, J=16.7 Hz), 4.09 (3H, s), 4.84 (1H, d, J=15.1 Hz), 5.52 (1H, d, J=15.1 Hz), 5.78 (1H, ddd, J=9.3, 8.3, 3.9 Hz), 6.95–7.1 (2H, m), 7.2–7.55 (7H, m), 7.6–7.8 (6H, m), 8.15 (1H, dd, J=7.6, 1.8 Hz), 9.88 (1H, br s).

Example 14

(3aR*,10aS*)-9-[4-(3-Methoxybenzamido)benzyl]-4-(phthalimidoacetyl)-2,3,3a,4,9,10a-hexahydrobenzo[b]cyclopenta[e][1,4]diazepin-10(1H)-one Using 3-methoxybenzoyl chloride, the title compound was synthesized in otherwise the same manner as Example 6. Yield 90%, m.p. 250.5°–251.3° C. (ethanol-diethyl ether).

¹H NMR (CDCl₃) δ: 1.0–1.5 (3H, m), 1.55–1.9 (2H, m), 2.0–2.25 (1H, m), 2.96 (1H, d, J=17.1 Hz), 3.13 (1H, dt, J=11.8, 9.0 Hz), 3.79 (1H, d, J=17.1 Hz), 3.83 (3H, s), 4.58 (1H, d, J=14.4 Hz), 5.65–5.85 (1H, m), 5.76 (1H, d, J=14.4 Hz), 7.0–7.1 (1H, m), 7.2–7.9 (15H, m), 8.31 (1H, br s).

Example 15

(3aR*,10aS*)-9-[4-(4-Methoxybenzamido)benzyl]-4-(phthalimidoacetyl)-2,3,3a,4,9,10a-hexahydrobenzo[b]cyclopenta[e][1,4]diazepin-10(1H)-one Using 4-methoxybenzoyl chloride, the title compound was synthesized in otherwise the same manner as Example 6. Yield 95%, m.p. 170°–173° C. (ethanol).

¹H NMR (CDCl₃) δ: 1.0–1.5 (3H, m), 1.55–1.9 (2H, m), 2.0–2.2 (1H, m), 3.00 (1H, d, J=16.4 Hz), 3.13 (1H, dt, J=11.7, 9.2 Hz), 3.81 (1H, d, J=16.4 Hz), 3.85 (3H, s), 4.62 (1H, d, J=14.6 Hz), 5.65–5.85 (1H, m), 5.71 (1H, d, J=14.6 Hz), 6.92 (2H, d, J=9.2 Hz), 7.2–7.4 (3H, m), 7.4–7.9 (11H, m), 8.30 (1H, br s).

Example 16

(3aR*,10aS*)-9-[4-(Phenylacetamido)benzyl]-4-(phthalimidoacetyl)-2,3,3a,4,9,10a-hexahydrobenzo[b]cyclopenta[e][1,4]diazepin-10(1H)-one Using phenylacetyl chloride, the title compound was synthesized in otherwise the same manner as Example 5. Yield 73%, m.p. 143°–145° C. (chloroform-ethanol).

¹H NMR (CDCl₃) δ: 1.0–1.45 (3H, m), 1.5–1.9 (2H, m), 2.0–2.2 (1H, m), 3.0–3.2 (1H, m), 3.01 (1H, d, J=16.6 Hz), 3.65 (2H, s), 3.82 (1H, d, J=16.6 Hz), 4.67 (1H, d, J=14.6 Hz), 5.57 (1H, d, J=14.6 Hz), 5.65–5.8 (1H, m), 7.15–7.5 (14H, m), 7.7–7.9 (4H, m).

Example 17

(3aR*,10aS*)-9-[4-(3-Phenylpropionamido)benzyl]-4-(phthalimidoacetyl)-2,3,3a,4,9,10a-hexahydrobenzo[b]cyclopenta[e][1,4]diazepin-10(1H)-one Using 3-phenylpropionyl chloride, the title compound was synthesized in otherwise the same manner as Example 6. Yield 87%, m.p. 222.1°–222.5° C. (ethanol-diethyl ether).

¹H NMR (CDCl₃) δ: 1.0–1.5 (3H, m), 1.55–1.9 (2H, m), 2.0–2.2 (1H, m), 2.5–2.7 (2H, m), 2.9–3.25 (4H, m), 3.82

Example 18
(3aR*,10aS*)-9-[4-(Phenoxyacetamido)benzyl]-4-(phthalimidoacetyl)-2,3,3a,4,9,10a-hexahydrobenzo[b]cyclopenta[e][1,4]diazepin-10(1H)-one Using phenoxyacetyl chloride, the title compound was synthesized in otherwise the same manner as Example 6. Yield 84%, m.p. 134°–137° C. (ethanol).

$^1$H NMR (CDCl$_3$) δ: 1.0–1.5 (3H, m), 1.5–1.9 (2H, m), 2.0–2.25 (1H, m), 3.05–3.25 (1H, m), 3.07 (1H, d, J=16.5 Hz), 3.88 (1H, d, J=16.5 Hz), 4.48 (1H, d, J=15.0 Hz), 4.58 (1H, d, J=15.0 Hz), 4.73 (1H, d, J=14.6 Hz), 5.59 (1H, d, J=14.6 Hz), 5.76 (1H, td, J=8.6, 3.6 Hz), 6.95–7.1 (3H, m), 7.2–7.5 (8H, m), 7.55 (2H, d, J=8.4 Hz), 7.6–7.8 (4H, m), 8.53 (1H, br s).

Example 19
(3aR*,10aS*)-9-[4-(Phenoxycarbonylamino)benzyl]-4-(phthalimidoacetyl)-2,3,3a,4,9,10a-hexahydrobenzo[b]cyclopenta[e][1,4]diazepin-10(1H)-one Using phenyl chloroformate, the title compound was synthesized in otherwise the same manner as Example 6. Yield 83%, m.p. 185°–187° C. (ethanol).

$^1$H NMR (CDCl$_3$) δ: 1.0–1.5 (3H, m), 1.55–1.9 (2H, m), 2.0–2.25 (1H, m), 3.05–3.25 (1H, m), 3.15 (1H, d, J=16.7 Hz), 3.91 (1H, d, J=16.7 Hz), 4.73 (1H, d, J=14.6 Hz), 5.58 (1H, d, J=14.6 Hz), 5.78 (1H, td, J=8.6, 3.9 Hz), 7.0–7.6 (14H, m), 7.6–7.9 (4H, m).

Example 20
(3aR*,10aS*)-9-[(4-Benzenesulfonamido)benzyl]-4-(phthalimidoacetyl)-2,3,3a,4,9,10a-hexahydrobenzo[b]cyclopenta[e][1,4]diazepin-10(1H)-one To a solution of (3aR*,10aS*)-9-(4-aminobenzyl)-4-(phthalimidoacetyl)-2,3,3a,4,9,10a-hexahydrobenzo[b]cyclopenta[e][1,4]diazepin-10(1H)-one hydrobromide (200 mg, 0.35 mmol) in 1,2-dichloroethane (30 mL) was added benzenesulfonyl chloride (61 mg, 0.35 mmol) as well as triethylamine (0.055 mL, 0.40 mmol) and the mixture was stirred at room temperature for 1.5 hours. After addition of saturated aqueous NaHCO$_3$ solution, the aqueous layer was separated and the organic layer was washed with saturated aqueous NaCl solution, dried over MgSO$_4$, and concentrated under reduced pressure to remove the solvent. The residue was crystallized from diethyl ether to provide 110 mg (yield 50%) of the title compound. m.p. 212°–214° C.

$^1$H NMR (CDCl$_3$) δ: 1.02–1.45 (3H, m), 1.55–1.91 (2H, m), 1.99–2.21 (1H, m), 2.91 (1H, d, J=16.8 Hz), 3.12 (1H, dt, J=11.8, 9.2 Hz), 3.79 (1H, d, J=16.8 Hz), 4.63 (1H, d, J=15.0 Hz), 5.59 (1H, d, J=15.0 Hz), 5.66–5.79 (1H, m), 6.90–7.57 (13H, m), 7.62–7.91 (5H, m).

Example 21
(3aR*,10aS*)-9-[4-(2-Naphthoylamino)benzyl]-4-(phthalimidoacetyl)-2,3,3a,4,9,10a-hexahyrobenzo[b]cyclopenta[e][1,4]diazepin-10(1H)-one Using 2-naphthoyl chloride, the title compound was synthesized in otherwise the same manner as Example 20. Yield 80%, m.p. 191°–194° C. (diethyl ether).

$^1$H NMR (CDCl$_3$) δ: 1.05–1.42 (3H, m), 1.51–1.90 (2H, m), 2.00–2.20 (1H, m), 2.99 (1H, d, J=16.4 Hz), 3.13 (1H, dt, J=11.4, 8.8 Hz), 3.80 (1H, d, J=16.4 Hz), 4.59 (1H, d, J=14.6 Hz), 5.68–5.81 (1H, m), 5.76 (1H, d, J=14.6 Hz), 7.23–7.93 (18H, m), 8.38 (1H, s), 8.47 (1H, s).

Example 22
(3aR*,10aS*)-9-(3-Benzamidobenzyl)-4-(phthalimidoacetyl)-2,3,3a,4,9,10a-hexahydrobenzo[b]cyclopenta[e]-[1,4]diazepin-10(1H)-one Using (3aR*,10aS*)-9-(3-aminobenzyl)-4-(phthalimidoacetyl)-2,3,3a,4,9,10a-hexahydrobenzo[b]cyclopenta[e][1,4]diazepin-10(1H)-one hydrobromide and benzoyl chloride, the title compound was synthesized in otherwise the same manner as Example 20. Yield 56%, m.p. 244°–246° C. (diethyl ether).

$^1$H NMR (CDCl$_3$) δ: 1.05–1.47 (3H, m), 1.52–1.92 (2H, m), 2.03–2.21 (1H, m), 3.18 (1H, dt, J=11.0, 8.4 Hz), 3.31 (1H, d, J=16.6 Hz), 4.13 (1H, d, J=16.6 Hz), 4.82 (1H, d, J=15.2 Hz), 5.61 (1H, d, J=15.2 Hz), 5.73–5.86 (1H, m), 7.03 (1H, d, J=6.8 Hz), 7.23–7.92 (16H, m), 8.33 (1H, br s).

Example 23
(3aR*,10aS*)-9-[4-(Benzylamino)benzyl]-4-(phthalimidoacetyl)-2,3,3a,4,9,10a-hexahydrobenzo[b]cyclopenta[e][1,4]diazepin-10(1H)-one To a suspension of (3aR*,10aS*)-9-(4-aminobenzyl)-4-(phthalimidoacetyl)-2,3,3a,4,9,10a-hexahydrobenzo[b]cyclopenta[e][1,4]diazepin-10(1H)-one (198 mg, 0.4 mmol) in chloroform (2 mL)-methanol (2 mL) was added benzaldehyde (49 μL, 0.48 mmol) and the mixture was stirred at room temperature for 40 minutes. To the resulting solution was added bromocresol green as well as sodium cyanoborohydride (30 mg, 0.48 mmol). Then, 10% HCl/methanol was added dropwise until the color of the mixture had ceased to change. This reaction mixture was stirred at room temperature for 15 minutes, at the end of which time it was diluted with water and extracted with 3 portions of chloroform. The pooled organic layer was washed with water, dried over MgSO$_4$, filtered, and concentrated under reduced pressure. The residue was crystallized from ethanol to provide 163 mg (Yield 70%) of the title compound. m.p. 178°–182° C.

$^1$H NMR (CDCl$_3$) δ: 1.0–1.5 (3H, m), 1.5–1.9 (2H, m), 2.0–2.2 (1H, m), 3.12 (1H, dt, J=11.7, 9.0 Hz), 3.29 (1H, d, J=16.5 Hz), 3.9–4.2 (1H, br), 3.91 (1H, d, J=16.5 Hz), 4.17 (1H, d, J=14.1 Hz), 4.26 (1H, d, J=14.1 Hz), 4.60 (1H, d, J=14.8 Hz), 5.54 (1H, d, J=14.8 Hz), 5.74 (1H, ddd, J=9.2, 8.2, 4.0 Hz), 6.58 (2H, d, J=8.4 Hz), 7.08 (2H, d, J=8.4 Hz), 7.1–7.5 (9H, m), 7.65–7.9 (4H, m).

Example 24
(3aR*,10aS*)-9-[4-(Benzylamino)benzyl]-4-(phthalimidoacetyl)-2,3,3a,4,9,10a-hexahydrobenzo[b]cyclopenta[e][1,4]diazepin-10(1H)-one hydrochloride In dichloromethane was dissolved (3aR*,10aS*)-9-[4-(benzylamino)benzyl]-4-(phthalimidoacetyl)-2,3,3a,4,9,10a-hexahydrobenzo[b]cyclopenta[e][1,4]diazepin-10(1H)-one followed by dropwise addition of 10% hydrogen chloridemethanol. The solution was concentrated under reduced pressure and the residue was crystallized from ethanol-diethyl ether to provide the title compound. m.p. 160°–165° C.

$^1$H NMR (DMSO-d$_6$) δ: 1.0–1.5 (3H, m), 1.5–1.9 (2H, m), 1.9–2.1 (1H, m), 3.0–3.2 (1H, m), 3.36 (1H, d, J=16.6 Hz), 4.10 (1H, d, J=16.6 Hz), 4.25 (2H, s), 4.9–5.15 (2H, m), 5.5–5.7 (1H, m), 6.7–6.9 (2H, m), 7.0–7.6 (11H, m), 7.8–8.0 (4H, m).

The amino proton resonance was too broad to be identified.

Example 25
(3aR*,10aS*)-9-[4-(3-benzylureido)benzyl]-4-(phthalimidoacetyl)-2,3,3a,4,9,10a-hexahydrobenzo[b]cyclopenta[e][1,4]diazepin-10(1H)-one To a solution of (3aR*,10aS*)-9-(4-aminobenzyl)-4-(phthalimidoacetyl)-2,3,3a,4,9,10a-hexahydrobenzo[b]cyclopenta[e][1,4]diazepin-10(1H)-one (148 mg, 0.3 mmol) in dichloromethane (4 mL) was added benzyl isocyanate (40

μL, 0.32 mmol) and the mixture was stirred at room temperature for 90 hours. After filtration, the reaction product was rinsed with diethyl ether to provide 118 mg (yield 63%) of the title compound. m.p. 169°–171° C.

$^1$H NMR (CDCl$_3$) δ: 1.0–1.5 (3H, m), 1.5–2.2 (3H, m), 2.95–3.15 (1H, m), 3.24 (1H, d, J=16.6 Hz), 4.32 (2H, d, J=5.6 Hz), 4.84 (1H, d, J=15.3 Hz), 4.93 (1H, d, J=16.6 Hz), 5.34 (1H, d, J=15.3 Hz), 5.6–5.8 (2H, m), 7.0–7.6 (14H, m), 7.6–7.9 (4H, m).

Example 26

(3aR*,10aS*)-9-[4-(3-Benzylureido)benzyl]-4-(2H-1,3-dioxo-1,3,4,5,6,7-hexahydroisoindole-2-acetyl)-2,3,3a,4,9,10a-hexahydrobenzo[b]cyclopenta[e][1,4]diazepin-10(1H)-one To a solution of (3aR*,10aS*)-9-(4-aminobenzyl)-4-(2H-1,3-dioxo-1,3,4,5,6,7-hexahydroisoindole-2-acetyl)-2,3,3a,4,9,10a-hexahydrobenzo[b]cyclopenta[e][1,4]diazepin-10(1H)-one (150 mg, 0.3 mmol) in chloroform (4 mL) was added benzyl isocyanate (40 μL, 0.32 mmol) and the mixture was stirred at room temperature for 6 hours. This reaction mixture was concentrated under reduced pressure and the residue was crystallized from ethyl acetate-diethyl ether to provide 96 mg (yield 51%) of the title compound. m.p. 168°–170° C.

$^1$H NMR (CDCl$_3$) δ: 1.0–1.5 (3H, m), 1.5–2.4 (11H, m), 2.9–3.15 (1H, m), 3.02 (1H, d, J=16.6 Hz), 3.71 (1H, d, J=16.6 Hz), 4.37 (2f1, d, J=6.0 Hz), 4.79 (1H, d, J=15.1 Hz), 5.33 (1H, d, J=15.1 Hz), 5.55–5.8 (2H, m), 7.0–7.5 (14H, m)

Example 27

(3aR*,10aS*)-9-[4-[3-((R)-1-Phenylethyl)ureido]-benzyl]-4-(phthalimidoacetyl)-2,3,3a,4,9,10a-hexahydrobenzo[b]cyclopenta[e][1,4]diazepin-10(1H)-one Using (3aR*,10aS*)-9-(4-aminobenzyl)-4-(phthalimidoacetyl)-2,3,3a,4,9,10a-hexahydrobenzo[b]cyclopenta[e][1,4]diazepin-10(1H)-one and (R)-1-phenylethyl isocyanate, the title compound was synthesized in otherwise the same manner as Example 26. Yield 54%, m.p. 158°–163° C. (ethyl acetate-diethyl ether).

$^1$H NMR (CDCl$_3$) δ: 1.0–1.5 (3H, m), 1.39, 1.44 (3H, dx2, J=6.8 Hz), 1.5–1.9 (2H, m), 2.0–2.2 (1H, m), 3.0–3.2 (1H, m), 3.20, 3.30 (1H, dx2, J=16.5 Hz), 3.83, 3.91 (1H, dx2, J=16.5 Hz), 4.5–5.0 (2H, m), 5.2–5.65 (2H, m), 5.75 (1H, td, J=8.6, 3.7 Hz), 6.6–7.6 (14H, m), 7.65–7.9 (4H, m).

Example 28

(3aR*,10aS*)-9-[4-[3-((S)-1-Phenylethyl)ureido]-benzyl]-4-(phthalimidoacetyl)-2,3,3a,4,9,10a-hexahydrobenzo[b]cyclopenta[e][1,4]diazepin-10(1H)-one Using (3aR*,10aS*)-9-(4-aminobenzyl)-4-(phthalimidoacetyl)-2,3,3a,4,9,10a-hexahydrobenzo[b]cyclopenta[e][1,4]diazepin-10(1H)-one and (S)-1-phenylethyl isocyanate, the title compound was synthesized in otherwise the same manner as Example 26. Yield 53%, m.p. 156°–160° C. (ethyl acetate-diethyl ether).

$^1$H NMR (CDCl$_3$) δ: 1.0–1.5 (3H, m), 1.40, 1.44 (3H, dx2, J=7.0 Hz), 1.5–1.9 (2H, m), 2.0–2.2 (1H, m), 3.0–3.2 (1H, m), 3.19, 3.30 (1H, dx2, J=16.4 Hz), 3.83, 3.90 (1H, dx2, J=16.5 Hz), 4.5–5.0 (2H, m), 5.2–5.7 (2H, m), 5.75 (1H, td, J=8.6, 3.9 Hz), 6.55–7.55 (141, m), 7.6–7.9 (4H, m).

Example 29

(3aR*,10aS*)-9-[4-(3-Benzyl-3-methylureido)benzyl]-4-(phthalimidoacetyl)-2,3,3a,4,9,10a-hexahydrobenzo[b]cyclopenta[e][1,4]diazepin-l0(1H)-one To a solution of (3aR*,10aS*)-9-[4-(3-benzyl-3-methylureido)benzyl]-2,3,3a,4,9,10a-hexahydrobenzo[b]cyclopenta[e][1,4]diazepin-10(1H)-one (0.30 g, 0.66 mmol) in dichloromethane (5 mL) was added bromoacetyl bromide (58 μL, 0.67 mmol) and the mixture was stirred at room temperature for 30 minutes. After addition of saturated aqueous NaHCO$_3$ solution, the aqueous layer was separated and extracted with dichloromethane. The pooled organic layer was washed with water, dried over MgSO$_4$, filtered, and concentrated under reduced pressure. The residue was subjected to silica gel column chromatography (hexane-ethyl acetate=1:11:2) to recover an amorphous fraction containing (3aR*,10aS*)-9-[4-(3-benzyl-3-methylureido)benzyl]-4-(bromoacetyl)-2,3,3a,4,9,10a-hexahydrobenzo[b]-cyclopenta[e][1,4]diazepin-10(1H)-one. This amorphous fraction was dissolved in DMF (1.5 mL) and after addition of potassium phthalimide (93 mg, 0.5 mmol), the solution was stirred at room temperature for 1.5 hours. This reaction mixture was diluted with water and extracted with 3 portions of ethyl acetate. The pooled organic layer was washed with water, dried over MgSO$_4$, filtered, and concentrated under reduced pressure. The residue was purified by silica gel column chromatography (hexane-ethyl acetate=2:11:11:2) and crystallized from ethyl acetate-diethyl ether to provide 57 mg (yield 13%) of the title compound. m.p. 156°–158° C.

$^1$H NMR (CDCl$_3$) δ: 1.0–1.45 (3H, m), 1.55–1.9 (2H, m), 2.0–2.2 (1H, m), 2.96 (3H ,s), 2.96 (1H, d, J=16.4 Hz), 3.12 (1H, dt, J=12.0, 9.1 Hz), 3.77 (1H, d, J=16.4 Hz), 4.51 (2H, s), 4.53 (1H, d, J=14.4 Hz), 5.65–5.8 (1H, rn), 5.72 (1H, d, J=14.4 Hz), 6.77 (1H, br s), 7.15–7.4 (10H, m), 7.4–7.5 (3H, m), 7.6–7.8 (4H, m).

Example 30

(3aR*,10aS*)-9-[4-[3-(2-Phenylethyl)ureido]benzyl]-4-(phthalimidoacetyl)-2,3,3a,4,9,10a-hexahydrobenzo[b]-cyclopenta[e][1,4]diazepin-10(1H)-one To a solution of (3aR*,10aS*)-4-(chloroacetyl)-9-[4-[3-(2-phenylethyl)ureido]benzyl]-2,3,3a,4,9,10a-hexahydrobenzo[b]cyclopenta[e][1,4]diazepin-10(1H)-one (53 mg, 0.1 mmol) in DMF (1 mL) was added potassium phthalimide (20 mg, 0.11 mmol) and the mixture was stirred at room temperature for 24 hours. This reaction mixture was diluted with ethyl acetate and water and the aqueous layer was extracted with ethyl acetate. The pooled organic layer was washed with water and saturated aqueous NaCl solution, dried over MgSO$_4$, filtered, and concentrated under reduced pressure. The residue was crystallized from ethanol-diethyl ether to provide 15 mg (yield 23%) of the title compound. m.p. 145°–147° C.

$^1$H NMR (CDCl$_3$) δ: 1.0–1.5 (3H, m), 1.55–1.9 (2H, m), 2.0–2.2 (1H, m), 2.77 (2H, t, J=7.1 Hz), 3.0–3.1 (1H, m), 3.16 (1H, d, J=16.6 Hz), 3.41 (2H, q, J=6.5 Hz), 3.89 (1H, d, J=16.6 Hz), 4.76 (1H, d, J=15.1 Hz), 5.01 (1H, t, J=5.8 Hz), 5.46 (1H, d, J=15.1 Hz), 5.75 (1H, td, J=8.6, 3.7 Hz), 6.82 (1H, br s), 7.0–7.6 (13H, m), 7.6–7.8 (4H, m).

Example 31

(3aR*,10aS*)-9-[4-[3-(4-Fluorobenzyl)ureido]benzyl]-4-(phthalimidoacetyl)- 2,3,3a,4,9,10a-hexahydrobenzo[b]-cyclopenta[e][1,4]diazepin-10(1H)-one Using (3aR*,10aS*)-4-(chloroacetyl)-9-[4-[3-(4-fluorobenzyl)ureido]benzyl]-2,3,3a,4,9,10a-hexahydrobenzo[b]cyclopenta[e][1,4]diazepin-10(1H)-one, the title compound was synthesized in otherwise the same manner as Example 30. Yield 35%, m.p. 154°–156° C. (ethanol-diethyl ether).

$^1$H NMR (CDCl$_3$) δ: 1.0–1.5 (3H, m), 1.5–1.9 (2H, m), 1.95–2.2 (1H, m), 2.95–3.2 (1H, m), 3.19 (1H, d, J=16.4 Hz), 3.91 (1H, d, J=16.4 Hz), 4.29 (2H, d, J=5.8 Hz), 4.79 (1H, d, J=15.0 Hz), 5.40 (1H, d, J=15.0 Hz), 5.6–5.8 (1H, m), 5.64 (1H, t, J=5.7 Hz), 6.89 (2H, t, J=8.6 Hz), 7.05–7.55 (11H, m), 7.6–7.8 (4H, m).

Example 32
(3aR*,10aS*)-9-[4-[3-(4-Methoxybenzyl)ureido]-benzyl]-4-(phthalimidoacetyl)-2,3,3a,4,9,10a-hexahydro-benzo[b]cyclopenta[e][1,4]diazepin-10(1H)-one Using (3aR*,10aS*)-4-(chloroacetyl)-9-[4-[3-(4-methoxybenzyl)ureido]benzyl]-2,3,3a,4,9,10a-hexahydro-benzo[b]cyclopenta[e][1,4]diazepin-10(1H)-one, the title compound was synthesized in otherwise the same manner as Example 30. Yield 38%, m.p. 155.5°–158.5° C. (ethanol-diethyl ether).

$^1$H NMR (CDCl$_3$) δ: 1.0–1.5 (3H, m), 1.5–1.9 (2H, m), 1.9–2.2 (1H, m), 2.9–3.15 (1H, m), 3.22 (1H, d, J=16.7 Hz), 3.74 (3H, s), 3.91 (1H, d, J=16.7 Hz), 4.25 (2H, d, J=5.4 Hz), 4.81 (1H, d, J=15.0 Hz), 5.37 (1H, d, J=15.0 Hz), 5.56 (1H, t, J=5.5 Hz), 5.6–5.8 (1H, m), 6.75 (2H, t, J=8.8 Hz), 6.9–7.6 (11H, m), 7.6–7.8 (4H, m).

Example 33
(3aR*,10aS*)-4-(Phthalimidoacetyl)-9-[4-[3-(4-pyridylmethyl)ureido]benzyl]-2,3,3a,4,9,10a-hexahydro-benzo[b]cyclopenta[e][1,4]diazepin-10(1H)-one To a solution of (3aR*,10aS*)-4-(Chloroacetyl)-9-[4-(phenoxycarbonylamino)benzyl]-2,3,3a,4,9,10a-hexahydrobenzo[b]cyclopenta[e][1,4]diazepin-10(1H)-one (151 mg, 0.3 mmol) in DMF (1.5 mL) was added 4-(aminomethyl)pyridine (30 μL, 0.3 mmol) and the mixture was stirred at room temperature for 44 hours. This reaction mixture was diluted with ethyl acetate and water, and the aqueous layer was extracted with 2 portions of ethyl acetate. The pooled organic layer was washed with water and saturated aqueous NaCl solution, dried over MgSO$_4$, filtered, and concentrated under reduced pressure. The residue was dissolved in DMF (2 mL) and after addition of potassium phthalimide (55 mg, 0.3 mmol), the mixture was stirred at room temperature for 90 hours. This reaction mixture was diluted with water and ethyl acetate and the aqueous layer was separated. The organic layer was washed with water and saturated aqueous NaCl solution, dried over MgSO$_4$, filtered, and concentrated under reduced pressure. The residue was purified by silica gel column chromatography (chloroform-methanol=20:1) to provide 33 mg (yield 17%) of the title compound. Amorphous.

$^1$H NMR (CDCl$_3$) δ: 1.0–1.5 (3H, m), 1.5–1.9 (2H, m), 1.9–2.2 (1H, m), 3.0–3.2 (1H, m), 3.11 (1H, d, J=16.5 Hz), 3.87 (1H, d, J=16.5 Hz), 4.37 (2H, d, J=6.0 Hz), 4.69 (1H, d, J=14.9 Hz), 5.2–5.8 (2H, m), 5.54 (1H, d, J=14.9 Hz), 6.9–7.6 (1H, m), 7.6–7.8 (4H, m), 8.4–8.5 (2H, m).

Example 34
(3aR*,10aS*)-4-(Phthalimidoacetyl)-9-[4-[3-(4-pyridylmethyl)ureido]benzyl]-2,3,3a,4,9,10a-hexahydrobenzo[b]cyclopenta[e][1,4]diazepin-10(1H)-one hydrochloride Using (3aR*,10aS*)-4-(phthalimidoacetyl)-9-[4-[3-(4-pyridylmethyl)ureido]benzyl]-2,3,3a, 4,9,10a-hexahydrobenzo[b]cyclopenta[e][1,4]diazepin-10(1H)-one, the title compound was synthesized in otherwise the same manner as Example 24. Amorphous.

$^1$H NMR (DMSO-d$_6$) δ: 1.0–2.2 (6H, m), 3.0–3.2 (1H, m), 3.2–3.6 (1H, m), 4.05–4.25 (1H, m), 4.3–4.6 (2H, m), 4.9–5.2 (2H, m), 5.9–6.1 (1H, m), 6.8–7.7 (10H, m), 7.7–8.0 (5H, m), 8.7–9.1 (3H, m).

The amino proton resonance was too broad to be identified.

The structural formulas of the compounds described in the above Examples are presented below.

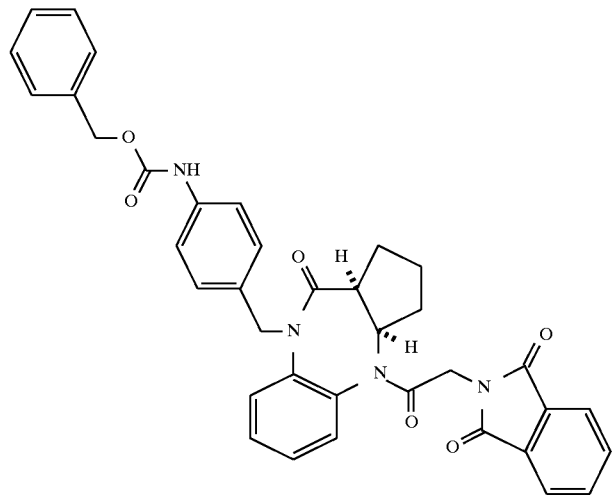

Example 1

-continued
Example 2
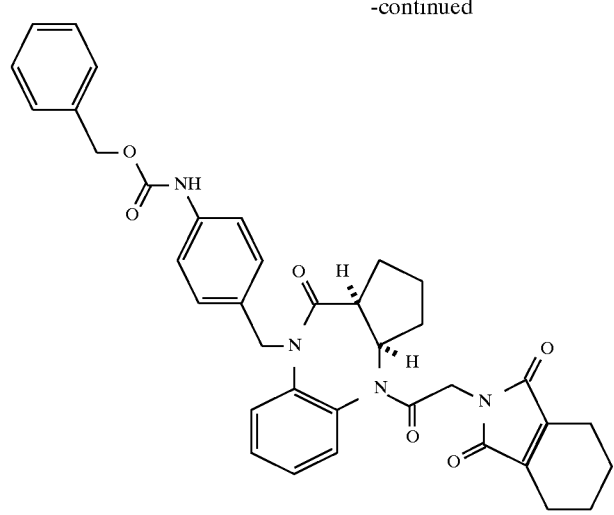
Example 3
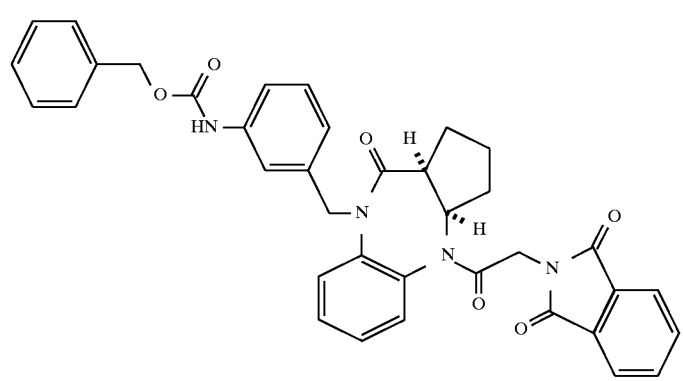
Example 4
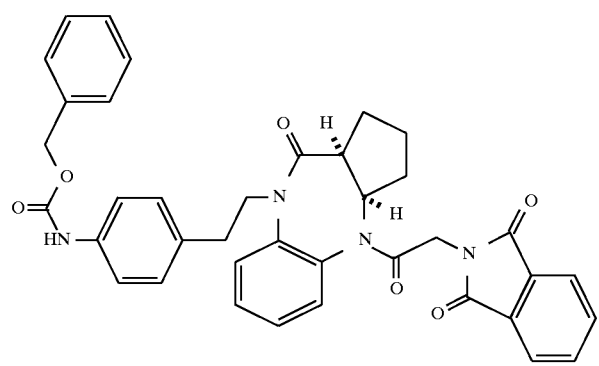
Example 5
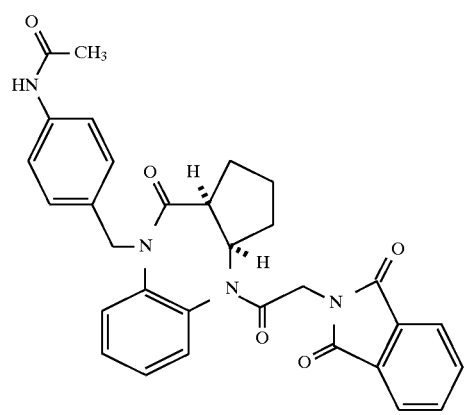

-continued
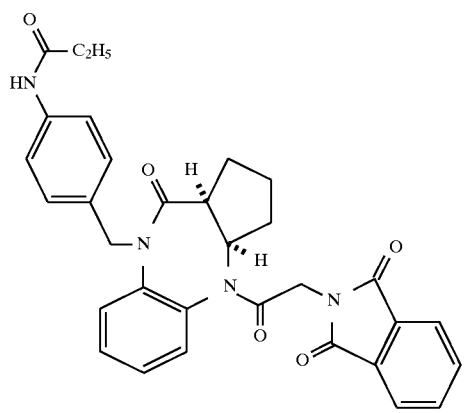
Example 6
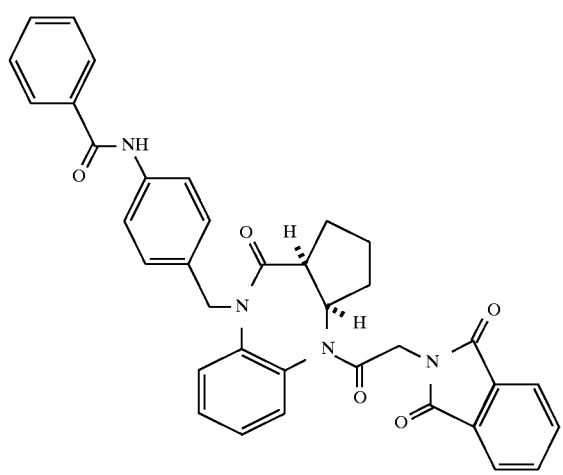
Example 7
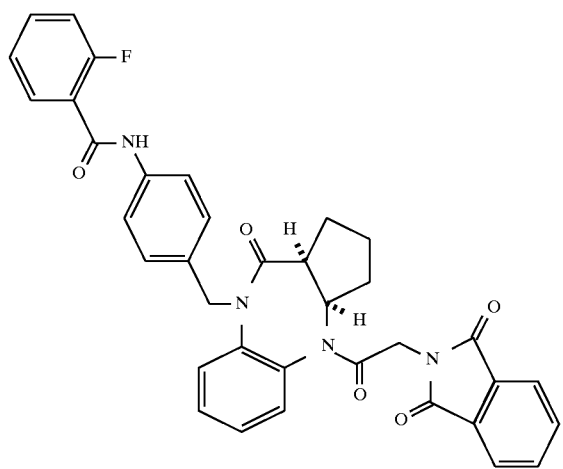
Example 8

-continued
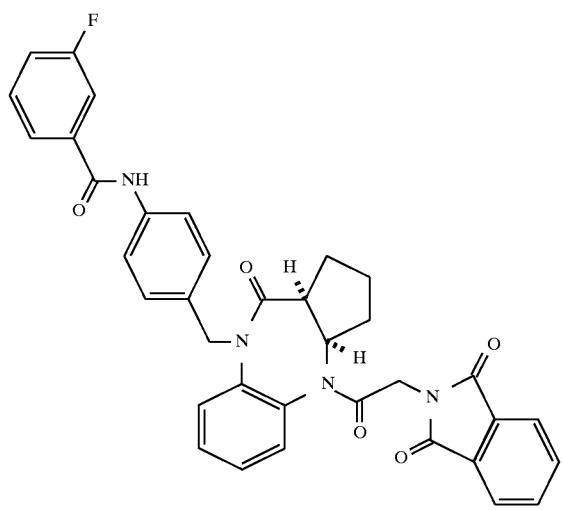
Example 9
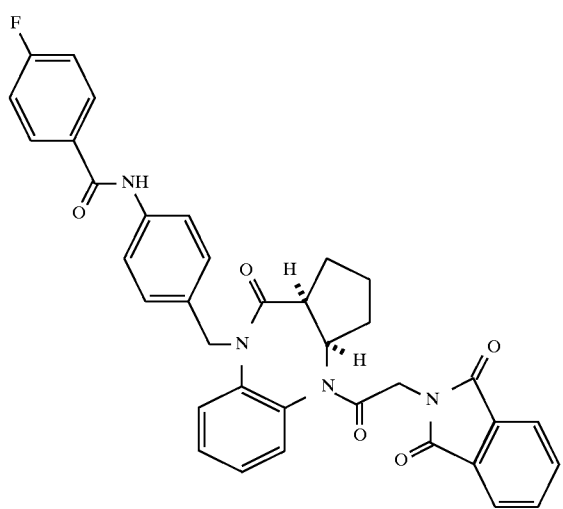
Example 10
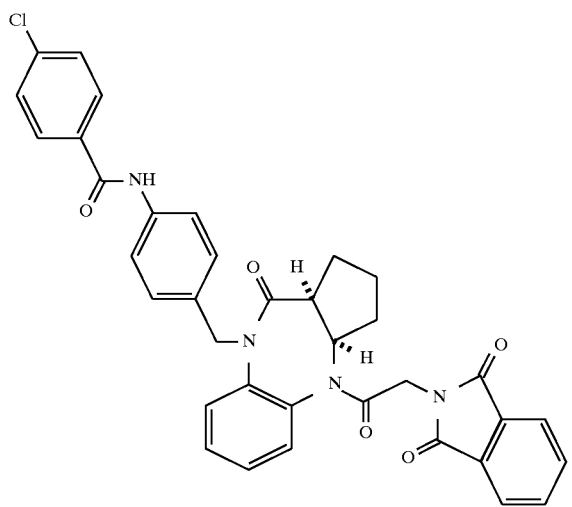
Example 11

-continued
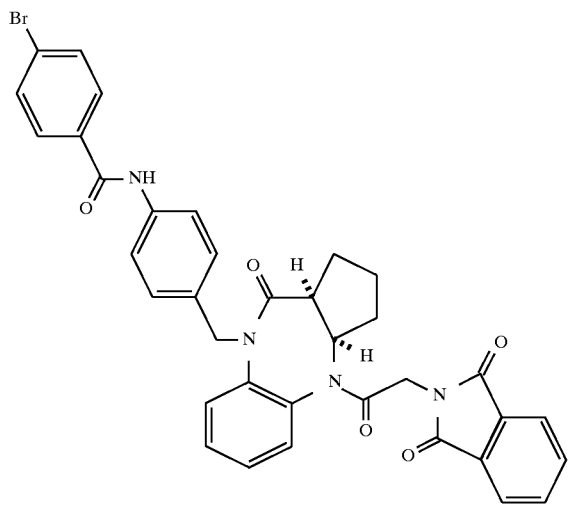
Example 12
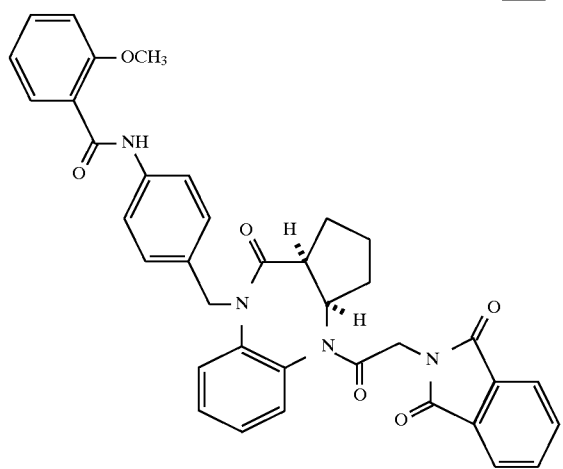
Example 13
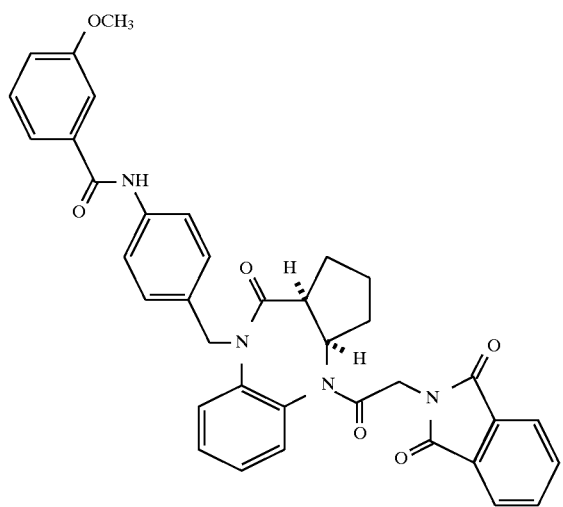
Example 14

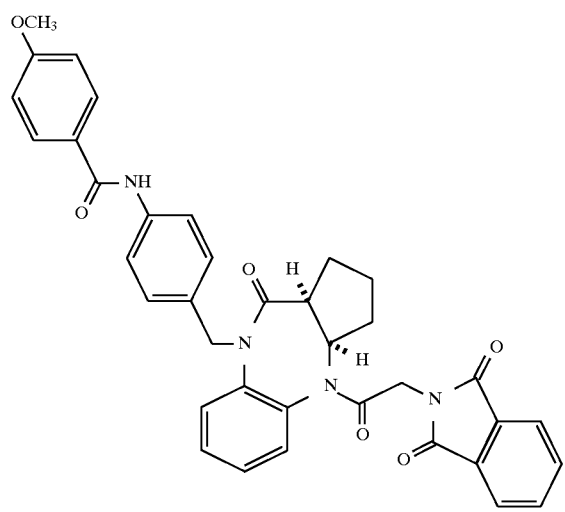
Example 15
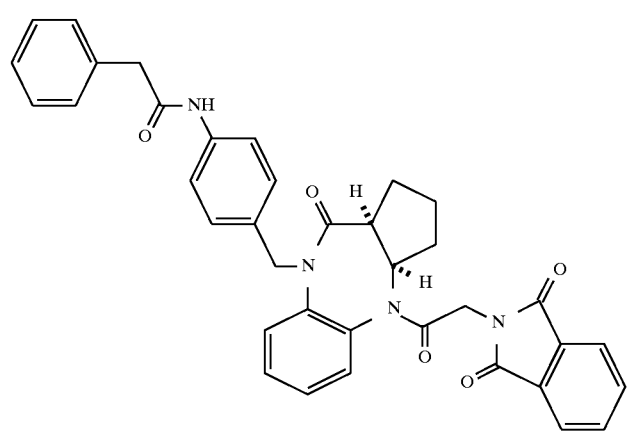
Example 16
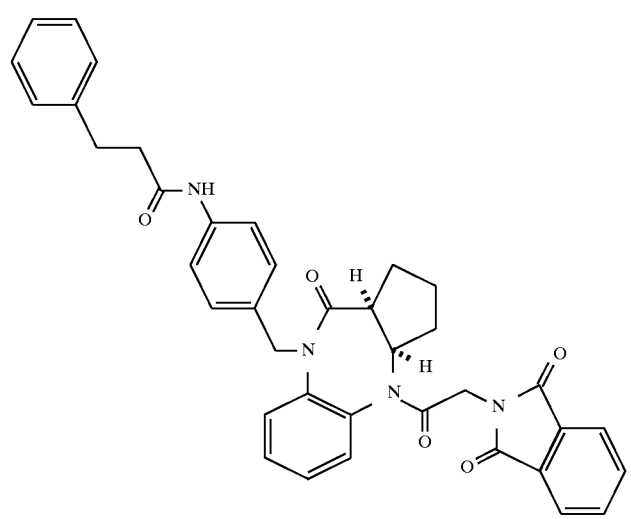
Example 17

-continued
Example 18
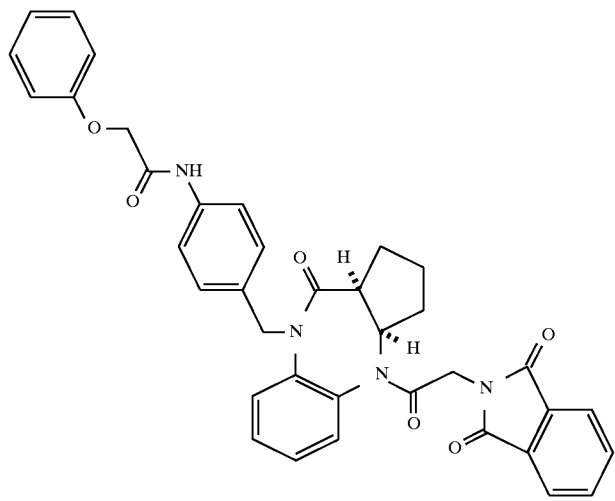
Example 19
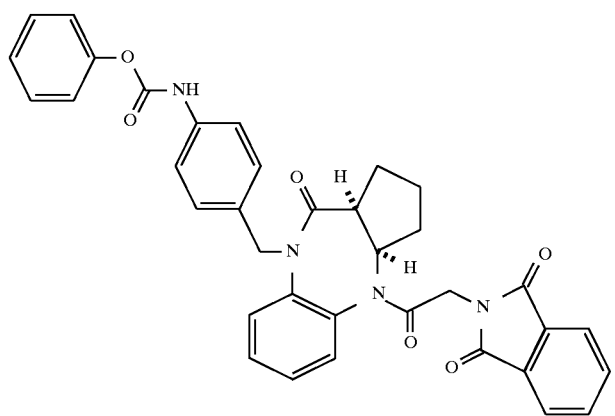
Example 20
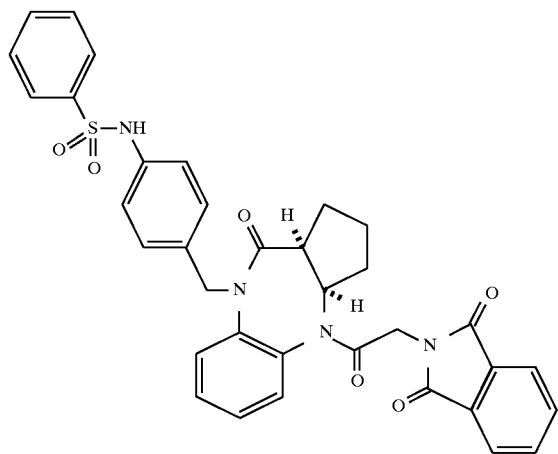

Example 21
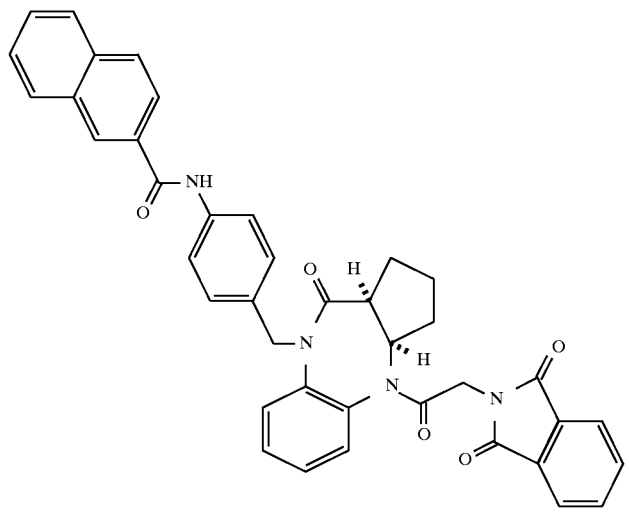
Example 22
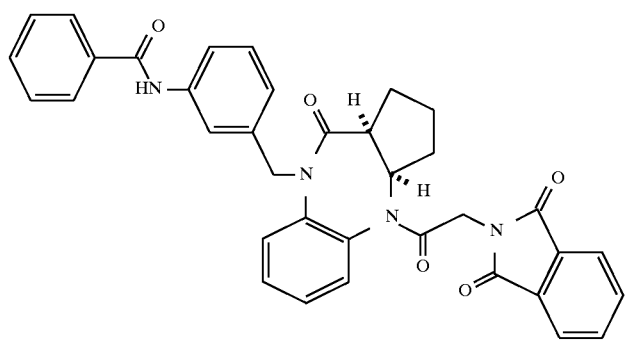
Example 23
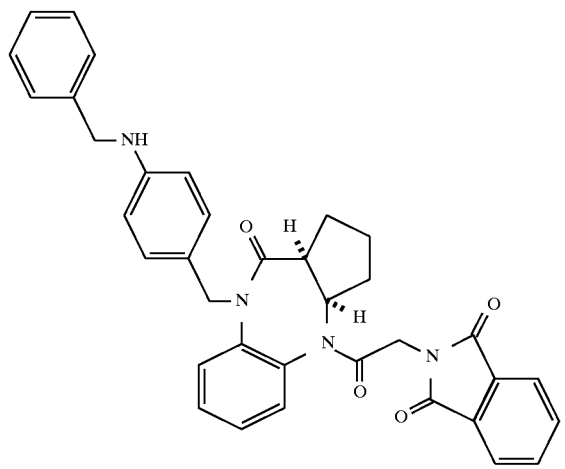

Example 24
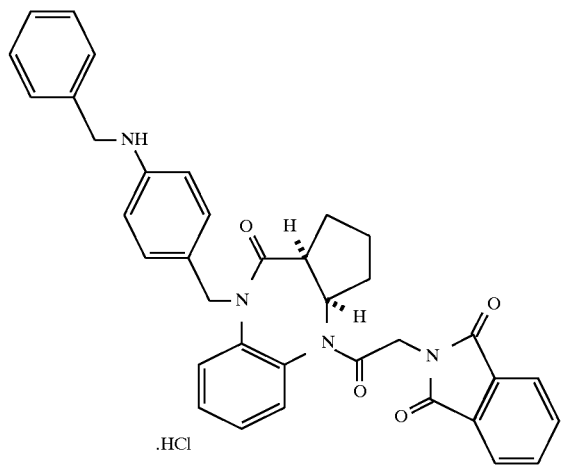
.HCl
Example 25
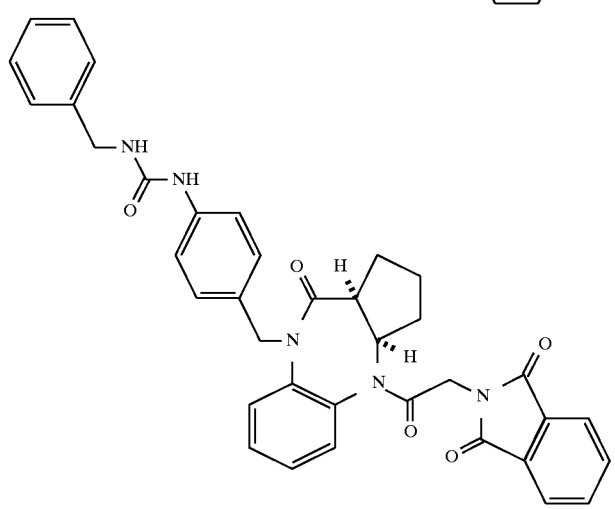
Example 26
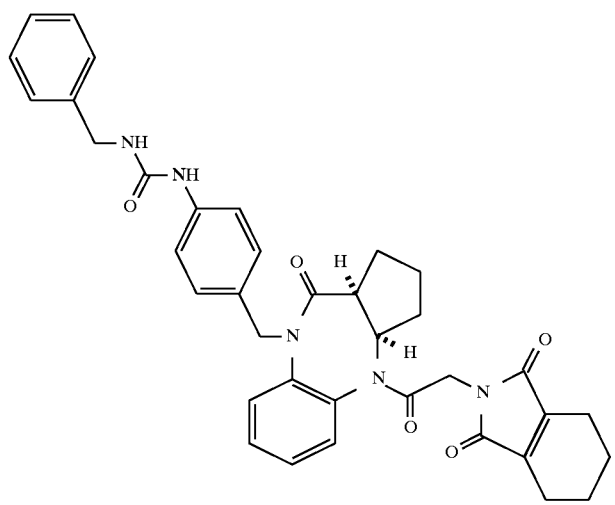

Example 27
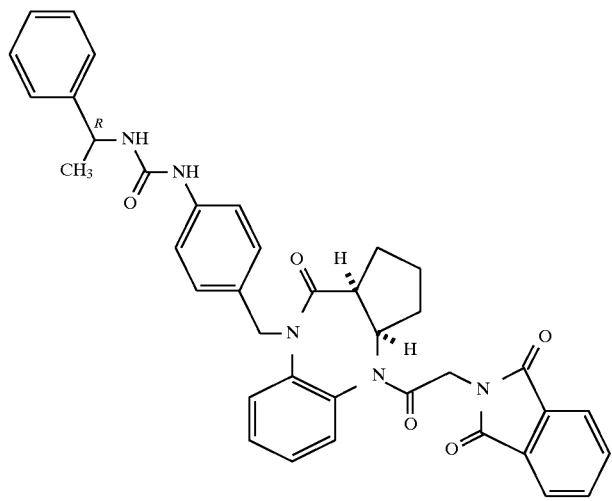
Example 28
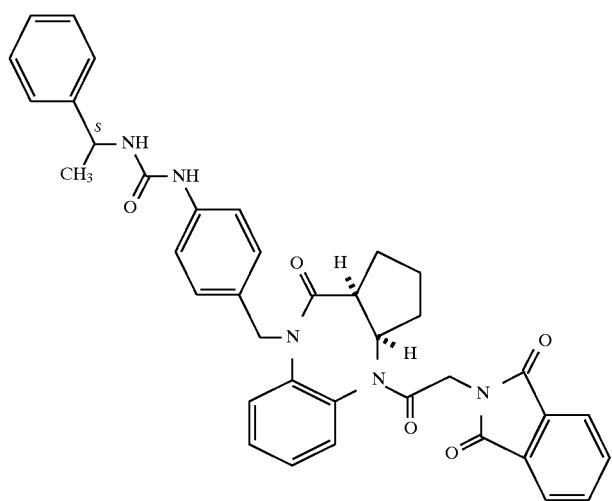
Example 29
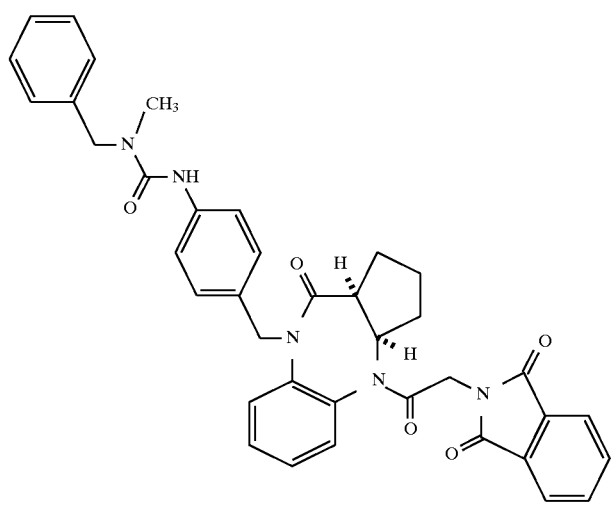

-continued
Example 30
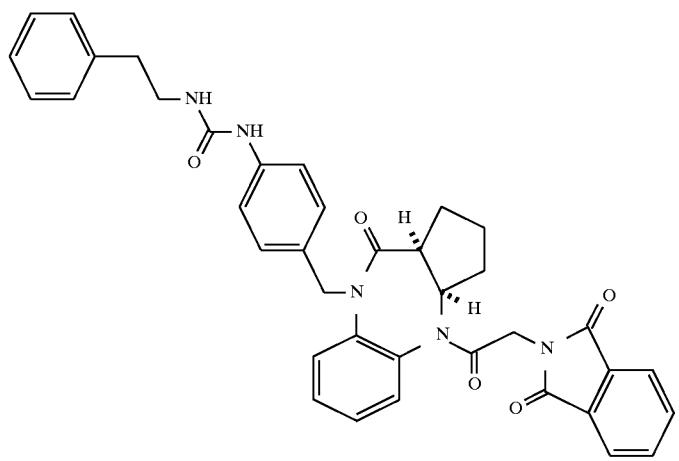
Example 31
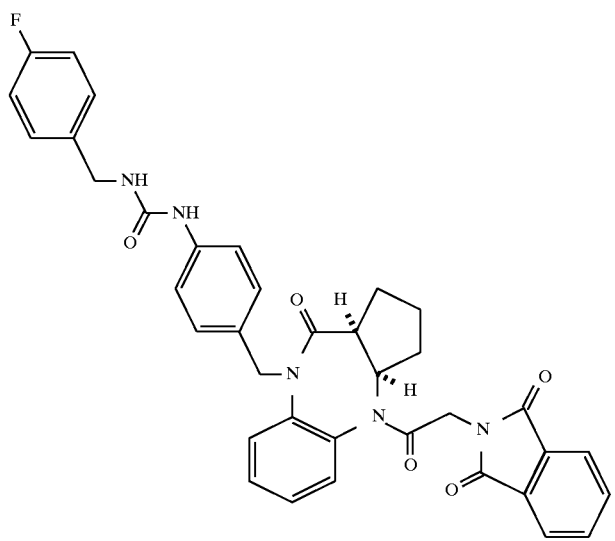
Example 32
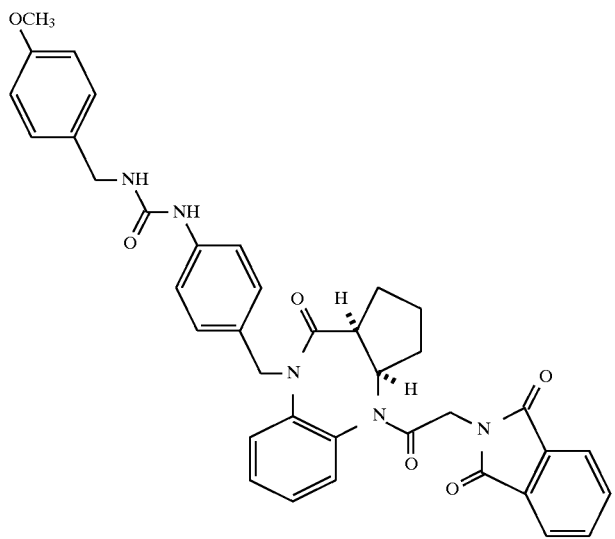

-continued

Example 33

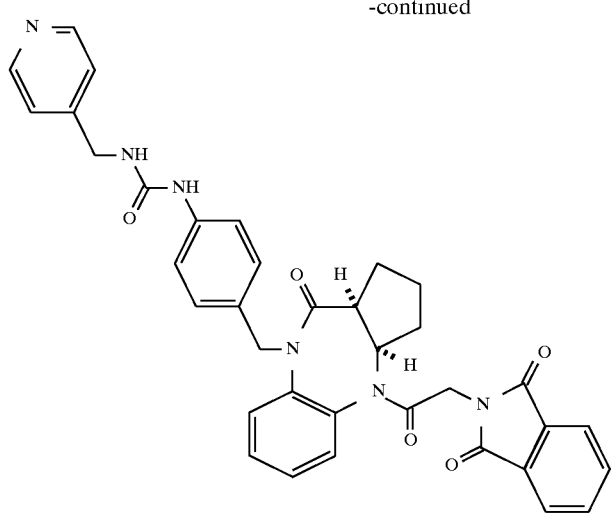

Example 34

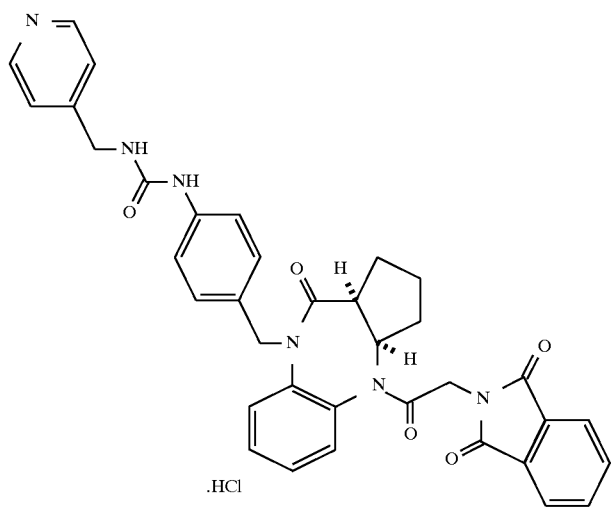

Preparation Example 1

| (1) Compound of Example 25 | 10.0 g |
|---|---|
| (2) Lactose | 60.0 g |
| (3) Corn starch | 35.0 g |
| (4) Gelatin | 3.0 g |
| (5) Magnesium stearate | 2.0 g |

A mixture of 10.0 g of the compound of Example 25, 60.0 g of lactose, and 35.0 g of corn starch was granulated with 30 ml of 10 weight % aqueous solution of gelatin (3.0 g as gelatin) through a 1 mm-mesh sieve, dried at 40° C., and resieved. The resulting granulation was admixed with 2.0 g of magnesium stearate and the mixture was compressed. The resulting bare tablets were coated with an aqueous suspension of sugar, titanium dioxide, talc, and gum arabic. The coated tablets were glazed with beeswax to provide 1000 finished tablets.

Preparation Example 2

| (1) Compound of Example 25 | 10.0 g |
|---|---|
| (2) Lactose | 70.0 g |
| (3) Corn starch | 50.0 g |
| (4) Soluble starch | 7.0 g |
| (5) Magnesium stearate | 3.0 g |

A mixture of 10.0 g of the compound of Example 25 and 3.0 g of magnesium stearate was granulated with 70 ml of aqueous soluble starch solution (7.0 g as soluble starch), dried, and admixed with 70.0 g of lactose and 50.0 g of corn starch. This mixture was compressed to provide 1000 tablets.

Experimental Example 1

Human GnRH receptor binding inhibition assay (A) Preparation of $^{125}$I-leuprolerin Ten (10) μl of $3\times10^{-4}$M aqueous leuprolerin solution and 10 μl of 0.01 mg/ml lactoperoxidase solution were taken in a tube, and 10 μl of Na$^{125}$I solution (37 MBq) was added. After stirring, 10 μl of 0.001% $H_2O_2$ was added and the reaction was conducted at room temperature for 20 minutes. The reaction was stopped by adding 700 μl of 0.05% TFA solution, and the reaction mixture was purified by reversed HPLC. The HPLC parameters are shown below. The retention time of $^{125}$I-leuprolerin was 26–27 minutes.

Column: TSKgel ODS-80™ CTR (4.6 mm×10 cm)

Eluent: Solvent A (0.05%TFA) Solvent B (40%CH$_3$CN-0.05%TFA)

Min. 0 (100% Solvent A)—Min. 3 (100% Solvent A)—Min. 7 (50% Solvent A+50% Solvent B)—Min. 40 (100% Solvent B) Elution temperature: room temperature Elution flow rate: 1 ml/min.

(B) Preparation of a CHO (Chinese hamster ovarian) cell membrane fraction containing human GnRH receptors CHO cells (10$^9$ cells) with human GnRH receptors expressed were floated on phosphate-buffered saline containing EDTA (PBS-EDTA) and centrifuged at 100×g for 5 minutes. To the pellet obtained was added 10 ml of a cell homogenate buffer (10 mM NaHCO$_3$, 5 mM EDTA, pH 7.5) and the mixture was homogenized using a Polytron homogenizer. The homogenate was centrifuged at 400×g for 15 minutes and the supernatant was taken in an ultracentrifuge tube and recentrifuged at 100,000×g for 1 hour. The membrane fraction thus obtained as a pellet was suspended in 2 ml of assay buffer and centrifuged at 100,000×g for 1 hour. The membrane fraction recovered was resuspended in 20 ml of assay buffer and the suspension was portioned, stored at −80° C., and thawed when needed.

(C) Determination of the $^{125}$I-leuprolerin binding inhibition rate

The membrane fraction prepared in Step (B) was diluted with assay buffer to 200 µg/ml and the dilution was portioned into tubes, 188 µl per tube. Then, 2 µl of 2 mM solution of the test compound in 60% DMSO and 10 µl of 38 nM $^{125}$I-leuprolerin solution in the same solvent were simultaneously added to the tubes. To determine the maximum binding, a test mixture of 2 µl of 60% DMSO and 10 µl of 38 nM $^{125}$I-leuprolerin solution in the same solvent was prepared. For the determination of nonspecific binding, a test mixture of 2 µl of 100 µM leuprolerin solution in 60% DMSO and 10 µl of 38 nM solution of $^{125}$I-leuprolerin in the same solvent was also prepared. The mixtures were respectively allowed to react at 25° C. for 60 minutes and the reaction product in each tube was filtered through a poly (ethylene imine)-treated Whatman glass filter (GF-F) under suction. The radioactivity of $^{125}$I-leuprolerin remaining on the filter was determined using a γ-counter.

Using the measured values, the following equation was calculated to find the binding inhibition rate for each test compound.

Binding inhibition (%)=(TB-SB)/(TB-NSB)×100

[SB: radioactivity with the compound added

TB: maximum bound radioactivity

NBS: nonspecifically bound radioactivity]

Using a concentration series of each test compound, the concentration of the compound which inhibited the binding by 50% (IC$_{50}$) was calculated by Hill plot. The results are presented in Table 1.

TABLE 1

Human GnRH receptor binding inhibition assay

| Compound Example No. | Binding inhibitory activity (IC$_{50}$, µM) |
|---|---|
| 1 | 0.1 |
| 2 | 0.07 |
| 6 | 0.8 |
| 7 | 0.2 |
| 8 | 0.3 |
| 9 | 0.2 |
| 10 | 0.2 |
| 11 | 0.2 |
| 12 | 0.3 |
| 14 | 0.2 |
| 15 | 0.2 |
| 17 | 0.5 |
| 18 | 0.6 |
| 21 | 0.2 |
| 25 | 0.03 |
| 26 | 0.04 |
| 27 | 0.02 |
| 28 | 0.3 |
| 30 | 0.04 |
| 31 | 0.03 |
| 32 | 0.04 |
| 34 | 0.08 |

It is apparent from Table 1 that the compound (I) and salt of the present invention have potent GnRH receptor antagonizing activity.

INDUSTRIAL APPLICABILITY

The compound (I) of the invention, inclusive of its salt, has potent GnRH receptor antagonizing activity and is sparingly toxic. Therefore, it can be safely used in man and other mammals (e.g. mouse, rat, rabbit, dog, bovine, swine, etc.) for such purposes as inhibition of ovulation and prevention of implantation or as a prophylactic-therapeutic agent for gonadotropin-dependent diseases such as amenorrhea, prostate cancer, prostatic hypertrophy, endometriosis, hysteromyoma, breast cancer, acne, precocious puberty, premenstrual syndrome, polycystic ovary syndrome, hyperandrogenism, hypopituitarism, etc. in human subjects.

Furthermore, the compound (I) of the present invention, inclusive of its salt, can be used as a contraceptive in men and women or as an ovulation inducing agent in women. Moreover, by using it in combination with a GnRH receptor agonist, the endogenic gonadotropins can be modulated and maintained at the proper levels so that an effective regimen for induction of ovulation can be provided.

The compound can also be used for modulation of the estrous cycle and promotion of growth in animals, improving of meat quality, and promotion of egg production in fish. Furthermore, it can be used in combination with a steroidal or non-steroidal antiandrogen. The compound (I) and salt of the invention feature a low toxic potential and a low risk of side effect.

We claim:
1. A compound of the formula:

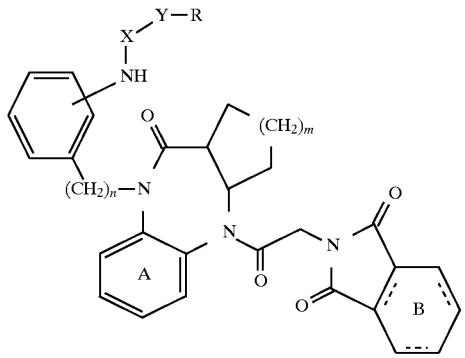

wherein Ring A represents a benzene ring which may be substituted by 1 to 3 substituents selected from the group consisting of an amino, mono-$C_{1-6}$ alkylamino, di-$C_{1-6}$ alkylamino, halogen, nitro, sulfo, cyano, hydroxy, $C_{1-6}$ alkyl, $C_{1-6}$alkoxy, carboxy, $C_{1-6}$ alkoxycarbonyl, formyl, acetyl, propionyl, mercapto and $C_{1-6}$ alkylmercapto, Ring B is a benzene, cyclohexene or cyclohexane group, each of which may be substituted by 1 to 3 substituents selected from the group consisting of an amino, mono-$C_{1-6}$ alkylamino, di-$C_{1-6}$ alkylamino, halogen, nitro, sulfo, cyano, hydroxy, $C_{1-6}$ alkyl, $C_{1-6}$ alkoxy, carboxy, $C_{1-6}$ alkoxy-carbonyl, formyl, acetyl, propionyl, mercapto and $C_{1-6}$ alkylmercapto;

- - - represents a single bond or a double bond;

X represents a lower alkylene, carbonyl or sulfonyl;

Y represents a bond, oxygen, lower alkyleneoxy or a group of the formula: >N—$R^1$ wherein $R^1$ represents hydrogen or an alkyl group;

R represents i) hydrogen,
  ii) (a) a $C_{6-14}$ aryl group or (b) a 5- to 10-membered heteroaromatic group containing, besides carbon atoms, 1 to 4 hetero atoms selected from the group consisting of nitrogen, oxygen and sulfur, each of which groups (a) and (b) may be substituted by 1 to 5 substituents selected from the group consisting of an amino, mono-$C_{1-6}$ alkylamino, di-$C_{1-6}$ alkylamino, halogen, nitro, sulfo, cyano, hydroxy, $C_{1-6}$ alkyl, $C_{1-6}$ alkoxy, carboxy, $C_{1-6}$ alkoxycarbonyl, formyl, acetyl, propionyl, mercapto, $C_{1-6}$ alkylmercapto and $C_{6-10}$ aryl, or
  iii) a $C_{1-6}$ alkyl group which may be substituted by 1 to 5 substituents selected from the group consisting of (a) a $C_{6-14}$ aryl group and (b) a 5- to 10-membered heteroaromatic group containing, besides carbon atoms, 1 to 4 hetero atoms selected from the group consisting of nitrogen, oxygen and sulfur, each of which groups (a) and (b) may be substituted by 1 to 5 substituents selected from the group consisting of an amino, mono-$C_{1-6}$ alkylamino, di-$C_{1-6}$ alkylamino, halogen, nitro, sulfo, cyano, hydroxy, $C_{1-6}$ alkyl, $C_{1-6}$ alkoxy, carboxy, $C_{1-6}$ alkoxycarbonyl, formyl, acetyl, propionyl, mercapto, $C_{1-6}$ alkylmercapto and $C_{6-10}$ aryl; and m and n independently represent an integer of 1 to 3, or a salt thereof.

2. A compound of claim 1 wherein X is a methylene, carbonyl or sulfonyl and Y is a bond, oxygen, methyleneoxy or a group of the formula: >N—$R^1$ wherein $R^1$ is as defined in claim 1.

3. A compound of claim 1 wherein X is a $C_{1-6}$ alkylene, carbonyl or sulfonyl, and Y is a bond, oxygen, $C_{1-6}$ alkyleneoxy or a group of the formula: >N—$R^1$ wherein $R^1$ is hydrogen or a $C_{1-6}$ alkyl group.

4. A compound of claim 1 wherein Ring A is an unsubstituted benzene ring.

5. A compound of claim 1 wherein Ring B is an unsubstituted ring.

6. A compound of claim 5 wherein Ring B is a benzene ring or a cyclohexene ring.

7. A compound of claim 1 wherein the (a) $C_{6-14}$ aryl group or (b) 5- to 10-membered heteroaromatic group containing, besides carbon atoms, 1 to 4 hetero atoms selected from the group consisting of nitrogen, oxygen and sulfur is a phenyl group or a pyridyl group.

8. A compound of claim 1 wherein R is i) a phenyl or naphthyl group optionally substituted by 1 to 3 substituents selected from the group consisting of a halogen and $C_{1-6}$ alkoxy or ii) a $C_{1-6}$ alkyl group optionally substituted by 1 to 3 substituents selected from the group consisting of a phenyl and pyridyl group, each of which may be substituted by 1 to 3 substituents selected from the group consisting of a halogen and $C_{1-6}$ alkoxy.

9. A compound of claim 1 wherein X is carbonyl.

10. A compound of claim 1 wherein Y is oxygen or the group of the formula: >N—$R^1$ wherein $R^1$ is as defined in claim 1.

11. A compound of claim 1 wherein Y is >NH.

12. A compound of claim 1 wherein the group of the formula: —NH—X—Y—R is present in the 3- or 4-position of the benzene ring.

13. A compound of claim 1 wherein m is 1.

14. A compound of claim 1 wherein n is 1.

15. A compound of claim 1 wherein Ring A is benzene ring,
Ring B is a benzene ring or a cyclohexene ring,
X is a methylene, carbonyl or sulfonyl,
Y is a bond, oxygen, methyleneoxy or a group of the formula: >N—$R^1$, wherein
$R^1$ is hydrogen or a $C_{1-6}$ alkyl group, and
R is i) a phenyl or naphthyl group optionally substituted by 1 to 3 substituents selected from the group consisting of a halogen and $C_{1-6}$ alkoxy, or
  ii) a $C_{1-6}$ alkyl group optionally substituted by 1 to 3 substituents selected from the group consisting of a phenyl and pyridyl group which may be substituted by 1 to 3 substituents selected from the group consisting of a halogen and $C_{1-6}$ alkoxy.

16. A compound of claim 1 which is (3aR*,10aS*)-9-[4-(benzyloxycarbonylamino)benzyl]-4-(2H-1,3-dioxo-1,3,4,5,6,7-hexahydroisoindole-2-acetyl)-2,3,3a,4,9,10a-hexahydrobenzo[b]cyclopenta[e][1,4]diazepin-10(1H)-one or a salt thereof.

17. A compound of claim 1 which is (3aR*,10aS*)-9-[4-(3-benzylureido)benzyl]-4-(phthalimidoacetyl)-2,3,3a,4,9,10a-hexahydrobenzo[b]cyclopenta[e][1,4]diazepin-10(1H)-one or a salt thereof.

18. A compound of claim 1 which is (3aR*,10aS*)-9-[4-(3-benzylureido)benzyl]-4-(2H-1,3-dioxo-1,3,4,5,6,7-hexahydroisoindole-2-acetyl)-2,3,3a,4,9,10a-hexahydrobenzo[b]cyclopenta[e][1,4]diazepin-10(1H)-one or a salt thereof.

19. A compound of claim 1 which is (3aR*,10aS*)-9-[4-[3-((R)-1-phenylethyl)ureido]benzyl]-4-(phthalimidoacetyl)-2,3,3a,4,9,10a-hexahydrobenzo[b]cyclopenta[e]-[1,4]diazepin-10(1H)-one or a salt thereof.

20. A compound of claim 1 which is (3aR*,10aS*)-9-[4-[3-(2-phenylethyl)ureido]benzyl]-4-(phthalimidoacetyl)-2,3,3a,4,9,10a-hexahydrobenzo[b]cyclopenta[e][1,4]diazepin-10(1H)-one or a salt thereof.

21. A compound of claim 1 which is (3aR*,10aS*)-9-[4-[3-(4-fluorobenzyl)ureido]benzyl]-4-(phthalimidoacetyl)-2,3,3a,4,9,10a-hexahydrobenzo[b]cyclopenta[e][1,4]diazepin-10(1H)-one or a salt thereof.

22. A compound of claim 1 which is (3aR*,10aS*)-9-[4-[3-(4-methoxybenzyl)ureido]benzyl]-4-(phthalimidoacetyl)-2,3,3a,4,9,10a-hexahydrobenzo[b]cyclopenta[e][1,4]diazepin-10(1H)-one or a salt thereof.

23. A compound of claim 1 which is (3aR*,10aS*)-4-(phthalimidoacetyl)-9-[4-[3-(4-pyridylmethyl)ureido]-benzyl]-2,3,3a,4,9,10a-hexahydrobenzo[b]cyclopenta[e]-[1,4]diazepin-10(1H)-one or a salt thereof.

24. A process for producing the compound of claim 1 which comprises one of the following steps:

i) a step of reacting a compound of the formula:

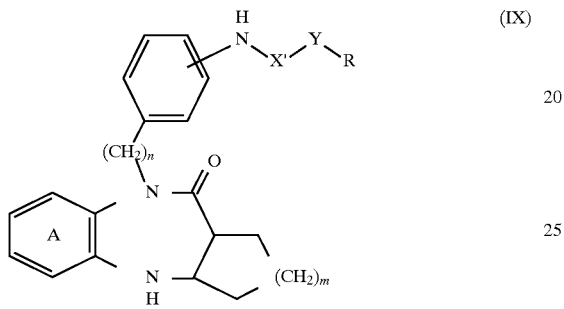

wherein X' represents carbonyl or sulfonyl and the other symbols are as defined in claim 1 or a salt thereof with a compound of the formula:

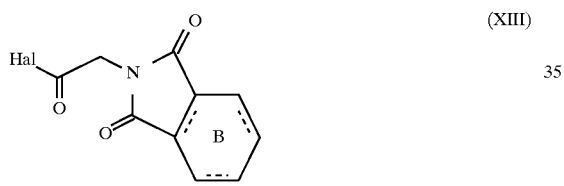

wherein Hal represents halogen and the other symbols are as defined in claim 1 or a salt thereof, ii) a step of reacting a compound of the formula:

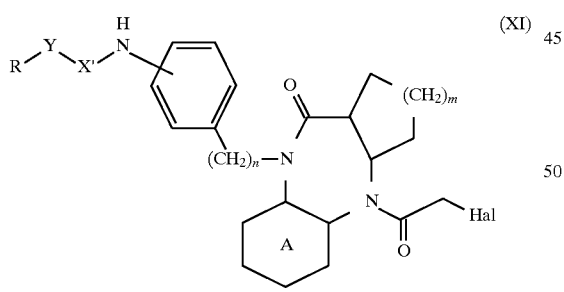

wherein each symbol is as defined above or a salt thereof with a compound of the formula:

wherein M represents a metal and the other symbols are as defined above or a salt thereof, iii) a step of reacting a compound of the formula:

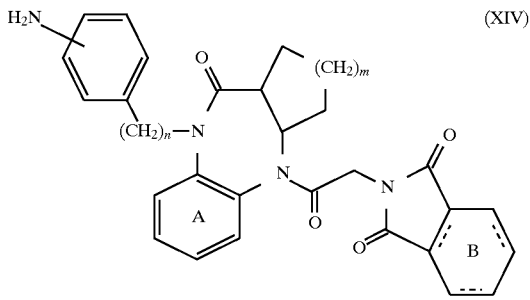

wherein each symbol is as defined above or a salt thereof with a compound of the formula:

wherein each symbol is as defined above or a salt thereof, iv) a step of reacting a compound of the formula:

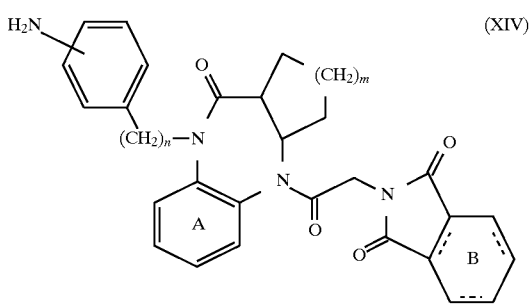

wherein each symbol is as defined above or a salt thereof with a compound of the formula:

wherein each symbol is as defined above or a salt thereof in the presence of a reducing agent, v) a step of reacting a compound of the formula:

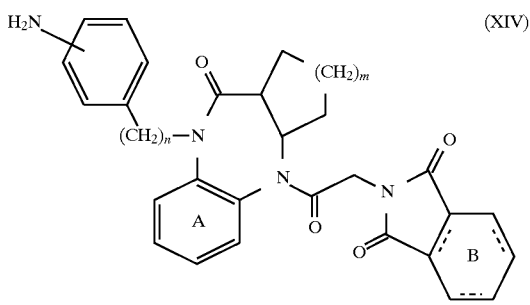

wherein each symbol is as defined above or a salt thereof with a compound of the formula:

RNCO    (XVII)

wherein R is as defined above or a salt thereof, and vi) a step of reacting a compound of the formula:

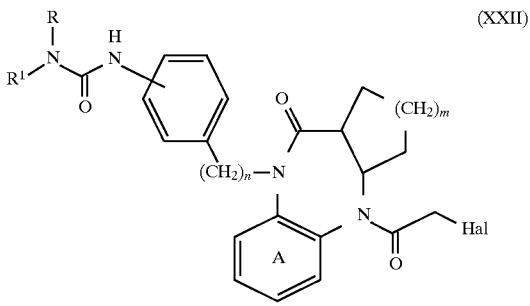

(XXII)

wherein each symbol is as defined above or a salt thereof with a compound of the formula:

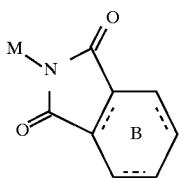

(XII)

wherein each symbol is as defined above or a salt thereof.

25. A pharmaceutical composition which comprises a compound of claim 1 with a pharmaceutically acceptable carrier.

26. Method for antagonizing gonadotropin releasing hormone receptor in mammals which comprises administrating to a subject in need a therapeutically effective amount of a compound of claim 1.

27. Method of claim 26 which is for sex hormone dependent diseases.

28. Method of claim 27 which is for treating tumors.

29. Method of claim 26 which is for controlling fertility.

30. Method of claim 26 which is for controlling menstrual cycle.

* * * * *

UNITED STATES PATENT AND TRADEMARK OFFICE
CERTIFICATE OF CORRECTION

PATENT NO.    :  5,866,567

DATED         :  February 2, 1999

INVENTOR(S)   :  SHIGENORI OHKAWA ET AL.

It is certified that error appears in the above-identified patent and that said Letters Patent is hereby corrected as shown below:

ON THE COVER PAGE AT [21], APPLICATION NO.

"666,430" should read --08/666,430--.

COLUMN 10

Line 6, "be" should be deleted.

COLUMN 17

Reaction Scheme 4, " 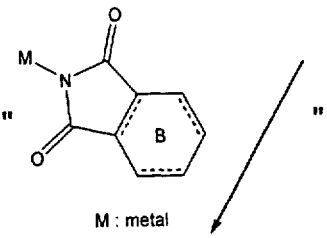 "

should read

-- 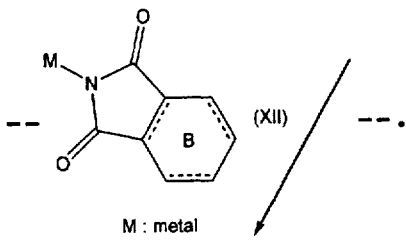 (XII) --.

COLUMN 19

Line 58, "20" should read --20°--.

UNITED STATES PATENT AND TRADEMARK OFFICE
CERTIFICATE OF CORRECTION

PATENT NO. : 5,866,567

DATED : February 2, 1999

INVENTOR(S) : SHIGENORI OHKAWA ET AL.

It is certified that error appears in the above-identified patent and that said Letters Patent is hereby corrected as shown below:

COLUMN 23

Line 4, "compoundd" should read --compound--.

COLUMN 31

Line 43, "7.1-7.5 (13H, m)" should read
--7.1-7.5 (13H, m).--;
Line 67, "7.59-7.85 (4H, m)" should read
--7.59-7.85 (4H, m).--.

COLUMN 37

Line 60, "6.55-7.55 (141, m)" should read
--6.55-7.55 (14H, m)--.

Signed and Sealed this

Twenty-ninth Day of May, 2001

Attest:

NICHOLAS P. GODICI

*Attesting Officer*     *Acting Director of the United States Patent and Trademark Office*